United States Patent
Vertes et al.

(10) Patent No.: US 8,901,487 B2
(45) Date of Patent: Dec. 2, 2014

(54) SUBCELLULAR ANALYSIS BY LASER ABLATION ELECTROSPRAY IONIZATION MASS SPECTROMETRY

(75) Inventors: Akos Vertes, Reston, VA (US); Jessica A. Stolee, Washington, DC (US); Bindesh Shrestha, Arlington, VA (US)

(73) Assignee: George Washington University, Washington, DC (US)

( * ) Notice: Subject to any disclaimer, the term of this patent is extended or adjusted under 35 U.S.C. 154(b) by 60 days.

(21) Appl. No.: 13/045,277

(22) Filed: Mar. 10, 2011

(65) Prior Publication Data

US 2011/0215233 A1    Sep. 8, 2011

Related U.S. Application Data

(63) Continuation-in-part of application No. 12/323,276, filed on Nov. 25, 2008, now Pat. No. 7,964,843, which is a continuation-in-part of application No. 12/176,324, filed on Jul. 18, 2008, now Pat. No. 8,067,730.

(60) Provisional application No. 60/951,186, filed on Jul. 20, 2007.

(51) Int. Cl.
  *H01J 49/00*    (2006.01)
  *H01J 49/26*    (2006.01)
  *H05H 3/02*    (2006.01)

(52) U.S. Cl.
  CPC . *H01J 49/26* (2013.01); *H05H 3/02* (2013.01)
  USPC .......................................... 250/288; 250/282

(58) Field of Classification Search
  USPC ........................... 250/282, 288, 251, 281, 285
  See application file for complete search history.

(56) References Cited

U.S. PATENT DOCUMENTS

| 5,338,930 | A | * | 8/1994 | Chu et al. ........................ 250/251 |
| 5,766,435 | A | * | 6/1998 | Liao et al. ........................ 204/451 |
| 5,965,884 | A |   | 10/1999 | Laiko et al. |
| 6,156,576 | A | * | 12/2000 | Allbritton et al. .............. 436/63 |

(Continued)

FOREIGN PATENT DOCUMENTS

| DE | 10310518 A1 | 10/2004 |
| JP | 2005-98909 A | 4/2005 |

(Continued)

OTHER PUBLICATIONS

Edwards et al., "Free-electron-laser-based biophysical and biomedical instrumentation", Review of Scientific Instruments, vol. 74, No. 7, Jul. 2003, pp. 3207-3245.

(Continued)

*Primary Examiner* — Nicole Ippolito
*Assistant Examiner* — Jason McCormack
(74) *Attorney, Agent, or Firm* — Fitch, Even, Tabin & Flannery LLP

(57) ABSTRACT

In various embodiments, a method of laser ablation electrospray ionization mass spectrometry (LAESI-MS) may generally comprise micro-dissecting a cell comprising at least one of a cell wall and a cell membrane to expose at least one subcellular component therein, ablating the at least one subcellular component by an infrared laser pulse to form an ablation plume, intercepting the ablation plume by an electrospray plume to form ions, and detecting the ions by mass spectrometry.

20 Claims, 25 Drawing Sheets

(56) References Cited

U.S. PATENT DOCUMENTS

| | | | |
|---|---|---|---|
| 6,495,824 B1 | 12/2002 | Atkinson | |
| 6,531,318 B1 | 3/2003 | Palmer-Toy et al. | |
| 6,548,263 B1* | 4/2003 | Kapur et al. | 506/32 |
| 6,558,946 B1 | 5/2003 | Krishnamurthy | |
| 6,656,690 B2 | 12/2003 | Crooke et al. | |
| 6,744,046 B2 | 6/2004 | Valaskovic et al. | |
| 6,949,741 B2 | 9/2005 | Cody et al. | |
| 6,991,903 B2 | 1/2006 | Fu et al. | |
| 7,084,396 B2 | 8/2006 | Schneider | |
| 7,091,483 B2 | 8/2006 | Fischer et al. | |
| 7,112,785 B2 | 9/2006 | Laramee et al. | |
| 7,129,483 B2 | 10/2006 | Youngquist et al. | |
| 7,170,052 B2 | 1/2007 | Furutani et al. | |
| 7,271,397 B2 | 9/2007 | Bryden et al. | |
| 7,335,897 B2 | 2/2008 | Takats et al. | |
| 7,345,275 B2 | 3/2008 | Amirav et al. | |
| 7,629,576 B2 | 12/2009 | Schultz et al. | |
| 7,684,934 B2 | 3/2010 | Shvartsburg et al. | |
| 7,687,772 B2 | 3/2010 | Shiea et al. | |
| 7,696,475 B2 | 4/2010 | Shiea et al. | |
| 7,714,276 B2 | 5/2010 | Pevsner et al. | |
| 7,735,146 B2 | 6/2010 | Vertes et al. | |
| 7,901,682 B2 | 3/2011 | Sabbadini | |
| 8,030,348 B2 | 10/2011 | Sampalis | |
| 2002/0190203 A1* | 12/2002 | Valaskovic et al. | 250/288 |
| 2003/0180801 A1* | 9/2003 | Maekawa et al. | 435/7.1 |
| 2004/0051037 A1* | 3/2004 | Taylor et al. | 250/288 |
| 2004/0121316 A1 | 6/2004 | Birkus et al. | |
| 2005/0029444 A1* | 2/2005 | Caprioli | 250/282 |
| 2005/0035284 A1* | 2/2005 | Schultz et al. | 250/287 |
| 2005/0048581 A1* | 3/2005 | Chiu et al. | 435/7.1 |
| 2005/0230615 A1* | 10/2005 | Furutani et al. | 250/287 |
| 2005/0230635 A1* | 10/2005 | Takats et al. | 250/424 |
| 2005/0247871 A1* | 11/2005 | Bryden et al. | 250/288 |
| 2005/0279929 A1* | 12/2005 | Youngquist et al. | 250/288 |
| 2006/0138317 A1* | 6/2006 | Schultz et al. | 250/287 |
| 2006/0190183 A1* | 8/2006 | Walden et al. | 702/19 |
| 2006/0217911 A1* | 9/2006 | Wang | 702/85 |
| 2007/0114375 A1* | 5/2007 | Pevsner et al. | 250/282 |
| 2007/0176113 A1* | 8/2007 | Shiea et al. | 250/423 P |
| 2007/0248947 A1 | 10/2007 | Cezar | |
| 2008/0006770 A1* | 1/2008 | Shiea | 250/288 |
| 2008/0020474 A1 | 1/2008 | Hayashizaki et al. | |
| 2008/0116366 A1* | 5/2008 | Shiea et al. | 250/282 |
| 2008/0124404 A1 | 5/2008 | Liu et al. | |
| 2008/0128614 A1 | 6/2008 | Nikolaev et al. | |
| 2008/0149822 A1* | 6/2008 | Vertes et al. | 250/282 |
| 2008/0220422 A1* | 9/2008 | Shoemaker et al. | 435/6 |
| 2008/0272294 A1* | 11/2008 | Kovtoun | 250/288 |
| 2008/0308722 A1 | 12/2008 | Shiea | |
| 2009/0027892 A1 | 1/2009 | Bremerich et al. | |
| 2009/0261243 A1 | 10/2009 | Bamberger et al. | |
| 2009/0272892 A1 | 11/2009 | Vertes et al. | |
| 2009/0272893 A1 | 11/2009 | Hieftje et al. | |
| 2009/0321626 A1 | 12/2009 | Vertes et al. | |
| 2010/0012831 A1 | 1/2010 | Vertes et al. | |
| 2010/0090101 A1 | 4/2010 | Schultz et al. | |
| 2010/0090105 A1 | 4/2010 | Liang et al. | |
| 2010/0252435 A1* | 10/2010 | Weber | 204/459 |
| 2010/0285446 A1 | 11/2010 | Vertes et al. | |
| 2011/0272572 A1 | 11/2011 | Vertes et al. | |
| 2012/0298857 A1 | 11/2012 | Vertes et al. | |

FOREIGN PATENT DOCUMENTS

| | | |
|---|---|---|
| WO | WO 96/32504 A2 | 10/1996 |
| WO | WO 99/45150 A1 | 9/1999 |
| WO | WO 00/52455 A1 | 9/2000 |
| WO | WO 00/77821 A2 | 12/2000 |
| WO | WO 01/25486 A1 | 4/2001 |
| WO | WO 02/055189 A2 | 7/2002 |
| WO | WO 02/070664 A2 | 9/2002 |
| WO | WO 02/071066 A1 | 9/2002 |
| WO | WO 02/095362 A2 | 11/2002 |
| WO | WO 03/093817 A2 | 11/2003 |
| WO | WO 03/100035 A2 | 12/2003 |
| WO | WO 2004/013602 A2 | 2/2004 |
| WO | WO 2004/044554 A2 | 5/2004 |
| WO | WO 2004/044555 A2 | 5/2004 |
| WO | WO 2004/076612 A2 | 9/2004 |
| WO | WO 2004/088271 A2 | 10/2004 |
| WO | WO 2004/097427 A1 | 11/2004 |
| WO | WO 2005/024046 A2 | 3/2005 |
| WO | WO 2005/031304 A2 | 4/2005 |
| WO | WO 2005/033271 A2 | 4/2005 |
| WO | WO 2006/014984 A1 | 2/2006 |
| WO | WO 2006/023398 A2 | 3/2006 |
| WO | WO 2006/026020 A2 | 3/2006 |
| WO | WO 2006/048642 A2 | 5/2006 |
| WO | WO 2006/054101 A2 | 5/2006 |
| WO | WO 2006/059123 A2 | 6/2006 |
| WO | WO 2006/061593 A2 | 6/2006 |
| WO | WO 2006/061625 A2 | 6/2006 |
| WO | WO 2006/064274 A2 | 6/2006 |
| WO | WO 2006/064280 A2 | 6/2006 |
| WO | WO 2006/067495 A2 | 6/2006 |
| WO | WO 2006/085110 A2 | 8/2006 |
| WO | WO 2006/129094 A2 | 12/2006 |
| WO | WO 2007/052025 A2 | 5/2007 |

OTHER PUBLICATIONS

Boskey, Adele and N. Camacho, "FT-IR Imaging of Native and Tissue-Engineered Bone and Cartilage", Biomaterials, May 2007, 28(15), pp. 2465-2478.

Cramer et al., "Matrix-assisted laser desorption and ionization in the O—H and C=O absorption bands of aliphatic and aromatic matrices: dependence on laser wavelength and temporal beam profile", International Journal of Mass Spectrometry and Ion Processes, 169/170, 1997, pp. 51-67.

Shrestha, Bindesh and Akos Vertes, "Ablation and analysis of small cell populations and single cells by consecutive laser pulses", Applied Physics A, presented at the 10th International Conference on Laser Ablation, 2008, Singapore, published online Jun. 3, 2010, 6 pages.

Stockle et al., "Nanoscale Atmospheric Pressure Laser Ablation-Mass Spectrometry", Analytical Chemistry, Apr. 1, 2001, vol. 73, No. 7, pp. 1399-1402.

Coon J. and Harrison W., "Laser Desorption-Atmospheric Pressure Chemical Ionization Mass Spectrometry for the Analysis of Peptides from Aqueous Solution", Analytical Chemistry, Nov. 1, 2002, vol. 74, No. 21, pp. 5600-5605.

Rasmussen et al., "New Dimension in Nano-Imaging: Breaking Through the Diffraction Limit with Scanning Near-Field Optical Microscopy", Anal Bioanal Chem., 2005, vol. 381, pp. 165-172.

Huang et al., "Direct Protein Detection from Biological Media through Electrospray-Assisted Laser Desorption Ionization/Mass Spectrometry", Journal of Proteome Research, vol. 5, No. 5, 2006, pp. 1107-1116.

Takats et al., "Mass Spectrometry Sampling Under Ambient Conditions with Desorption Electrospray Ionization", Science Magazine, vol. 306, Oct. 15, 2004, pp. 471-473.

Cody et al., "Versatile New Ion Source for the Analysis of Materials in Open Air under Ambient Conditions", Analytical Chemistry, vol. 77, No. 8, Apr. 15, 2005, pp. 2297-2302.

Nemes, Peter and Akos Vertes, "Laser Ablation Electrospray Ionization for Atmospheric Pressure, in Vivo and Imaging Mass Spectrometry", Analytical Chemistry, Nov. 1, 2007, vol. 79, No. 21, American Chemical Society, published on Web Sep. 27, 2007, pp. 8098-8106.

Moffit et al., Recent Advances in Optical Tweezers, Annual Review of Biochemistry, 2008, vol. 77, pp. 205-228.

Nemes et al. "Simultaneous imaging of Small Metabolites and Lipids in Rat Brain Tissues at Atmosphereic Pressure by Laser Ablation Electrospray Ionization Mass Spectrometry", Analytical Chemistry, vol. 82, No. 3, Feb. 1, 2010, pp. 982-988.

Shrestha, Bindesh and Akos Vertes, "In Situ Metabolic Profiling of Single Cells by Laser Ablation Electrospray Ionization Mass Spectrometry", Analytical Chemistry, vol. 81, No. 20, Oct. 15, 2009, pp. 8265-8271.

(56) References Cited

OTHER PUBLICATIONS

Sampson et at, "Intact and Top-Down Characterization of Biomolecules and Direct Analysis Using Infrared Matrix-Assisted Laser Desorption Electrospray Ionization Coupled to FT-ICR Mass Spectrometry", Journal of the American Society for Mass Spectrometry, 2009, vol. 20, pp. 667-673.

Rezenorn, at al., "Infrared laser-assisted desorption electrospray ionization mass spectrometry", The Analyst, 2008, vol. 133, pp. 226-232.

"Generation of three-dimensional images in mass spectrometry", Technology Access offered by Hessische Intellectual Property Offensive, TransMIT Society for Technology Transfer Department of Patents and Innovations, May 16, 2003, printed from http://www.hipo-online.de/files/Exp_Hipo_3D_MS_EN_160503.pdf, 2 pages.

Nemes et al., "Three-Dimensional Imaging of Metabolites in Tissues under Ambient Conditions by Laser Ablation Electrospray Ionization Mass Spectrometry", Analytical Chemistry, Aug. 15, 2009, vol. 81, No. 16, pp. 6668-6675.

Nemes et al., "Ambient Molecular Imaging and Depth Profiling of Live Tissue by Infrared Laser Ablation Electrospray Ionization Mass Spectrometry", Analytical Chemistry, Jun. 15, 2008, vol. 80, No. 12, pp. 4575-4582.

Vaikkinen et al., "Infrared Laser Ablation Atmospheric Pressure Photoionization Mass Spectrometry", Analytical Chemistry, 2012, 84, 1630-1636.

Meyerhoff et al., "Elevated subcortical choline metabolites in cognitively and clinically asymptomatic HIV patients", Neurology, Mar. 1, 1999, vol. 52, No. 5, 995, 3 pages.

Rhodes et al., "Metabolic Abnormalities Associated with Diabetes Mellitus, as Investigated by Gas Chromatography and Pattern-Recognition Analysis of Profiles of Volitile Metabolites", Clinical Chemistry, vol. 27, No. 4, 1981, pp. 580-585.

Jung Woo, Product Brochure "Ion LMD Pro—The Cutting Edge, Image Oriented Navigation Laser Microdissection Device," F&B Factory & Bio Mechanics, 12 pages.

P.A.L.M. Microlaser Technologies (A Company of Carl Zeiss Group), Product Brochure: "PALM Microbeam Moving Worlds—Non-contact Microdissection for Pure DNA, RNA, Proteins and Living Cells," Microlaser Technologies, 26 pages.

Emmert-Buck et al., "Laser Capture Microdissection," Science, vol. 274, Nov. 8, 1996, pp. 998-1001.

Jung Woo, Product Brochure "Ion LMD Pro—The Cutting Edge, Image Oriented Navigation Laser Microdissection Device," F&B Factory & Bio Mechanics, 12 pages, 2013.

P.A.L.M. Microlaser Technologies (A Company of Carl Zeiss Group), Product Brochure: "PALM Microbeam Moving Worlds—Non-contact Microdissection for Pure DNA, RNA, Proteins and Living Cells," Microlaser Technologies, 26 pages, Nov. 2005.

* cited by examiner

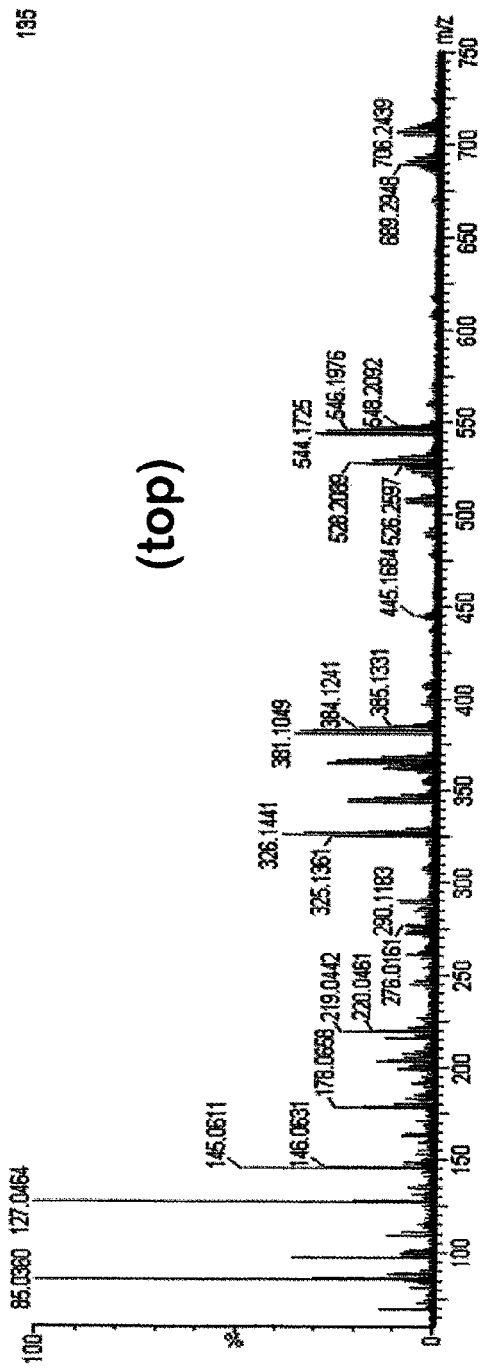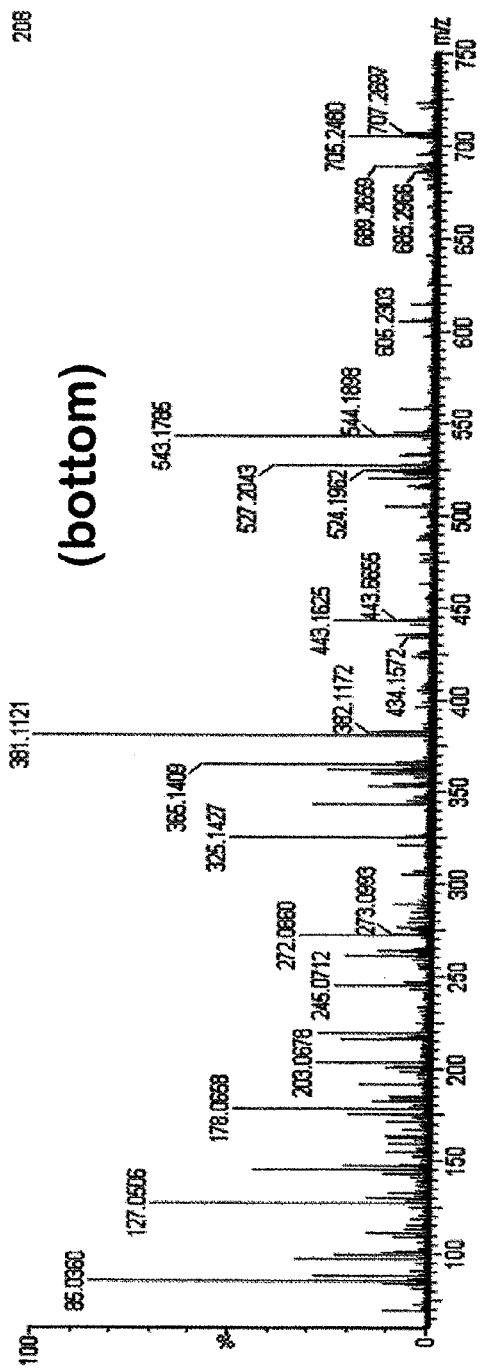
FIG. 9A

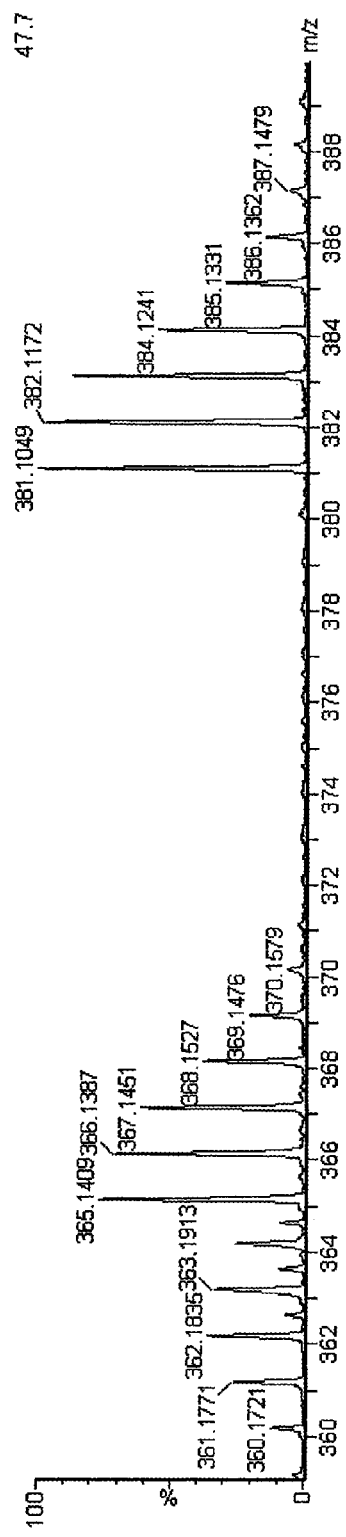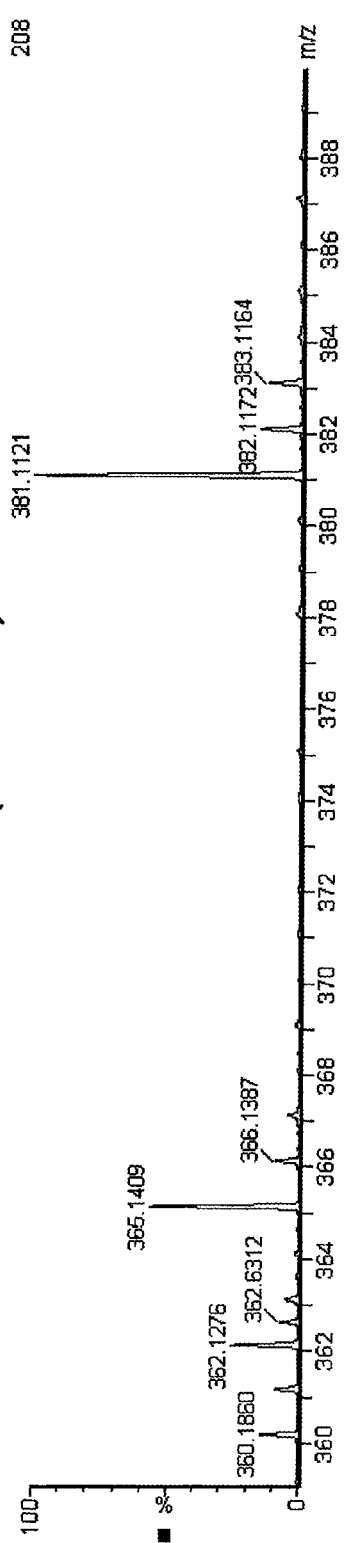
FIG. 9B

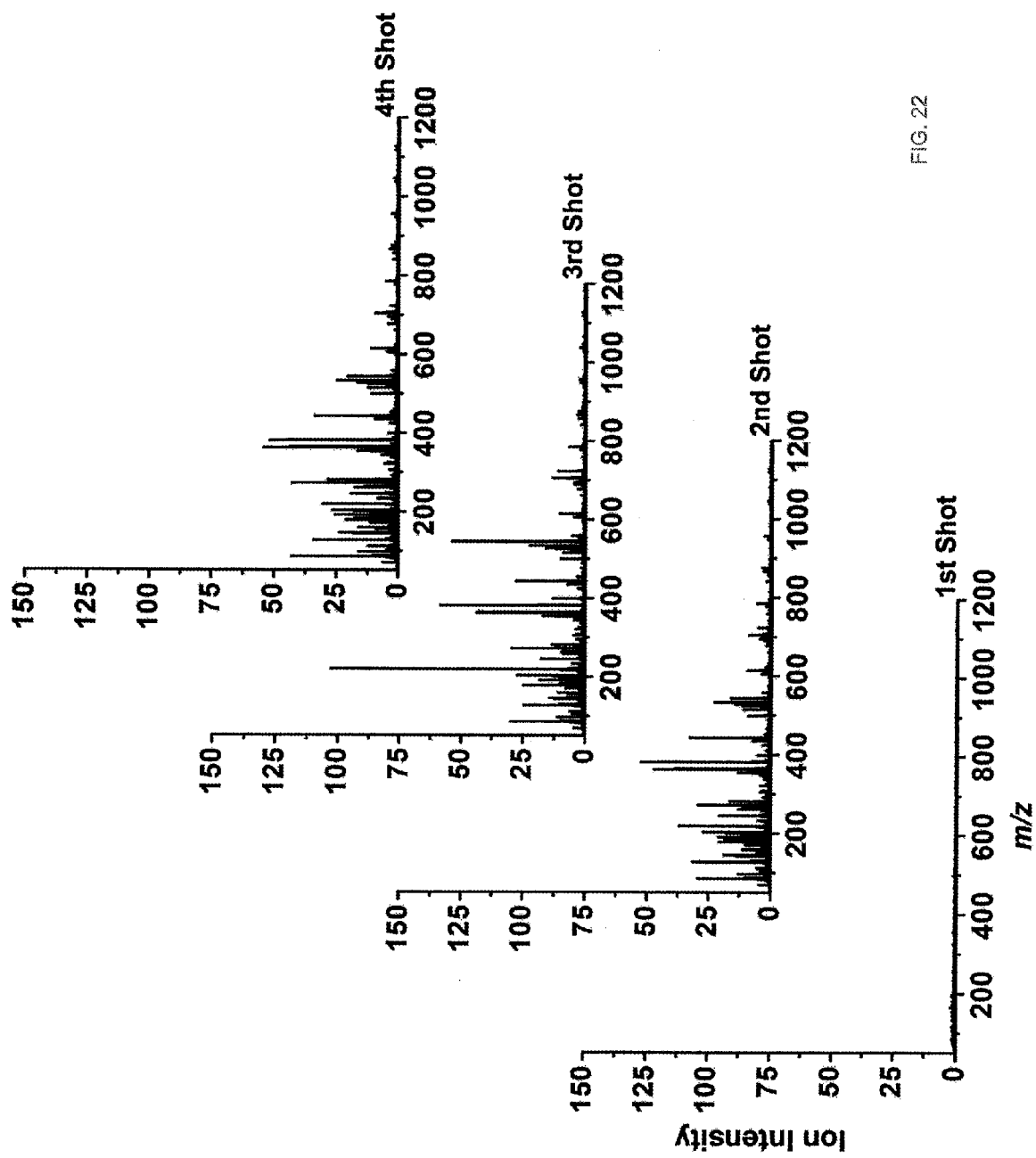

US 8,901,487 B2

SUBCELLULAR ANALYSIS BY LASER ABLATION ELECTROSPRAY IONIZATION MASS SPECTROMETRY

CROSS-REFERENCE TO RELATED APPLICATIONS

This is a continuation-in-part of U.S. application Ser. No. 12/323,276, filed on Nov. 25, 2008 now U.S. Pat. No. 7,964,834, which is a continuation-in-part of U.S. application Ser. No. 12/176,324, filed on Jul. 18, 2008 now U.S. Pat. No. 8,067,730, which claims priority to U.S. provisional application Ser. No. 60/951,186, filed on Jul. 20, 2007, each of the foregoing applications are hereby incorporated herein by reference in their entireties.

STATEMENT OF GOVERNMENTAL INTEREST

Portions of this invention were made with United States government support under Grant No. 0719232 awarded by the National Science Foundation and Grant No. DEFG02-01ER15129 awarded by the Department of Energy. The government has certain rights in the invention.

BACKGROUND

The apparatuses and methods described herein generally relate to ionization sources for mass spectrometers and methods of mass spectrometry, and in particular, laser ablation electrospray ionization (LAESI) mass spectrometry (MS), as well as methods of making and using the same.

Mass spectrometry is an analytical technique that has been successfully used in chemistry, biology, and other fields for qualitative and quantitative analysis. The analysis of single cells and subcellular components by conventional methods of mass spectrometry may be problematic. For example, matrix-assisted laser desorption ionization (MALDI) may suffer from time consuming and complex sample preparation, and in situ analysis of a sample under vacuum may be difficult. MALDI also utilizes a matrix that may interfere with the analysis of single cells and subcellular components. Mass spectrometry may be combined with separation techniques, such as capillary electrophoresis and fractionation, however, these techniques may increase the analysis time, complexity and/or cost. These conventional methods, however, may cause environmental perturbations that may affect the composition of the cell and/or subcellular components.

Accordingly, more efficient and/or cost-effective ionization sources for mass spectrometers and methods of making and using the same are desirable.

DESCRIPTION OF THE DRAWINGS

The various embodiments described herein may be better understood by considering the following description in conjunction with the accompanying drawings.

FIGS. 9A-C include representative mass spectra corresponding to a deuterium oxide ($D_2O$) treated *A. cepa* epidermal cell (top) and an untreated *A. cepa* epidermal cell (bottom) according to various embodiments described herein.

FIG. 22 includes representative mass spectra of a single *A. cepa* epidermal cell generated by consecutive laser pulses without cell dissection according to various embodiments described herein.

DESCRIPTION OF CERTAIN EMBODIMENTS

Figure 1:
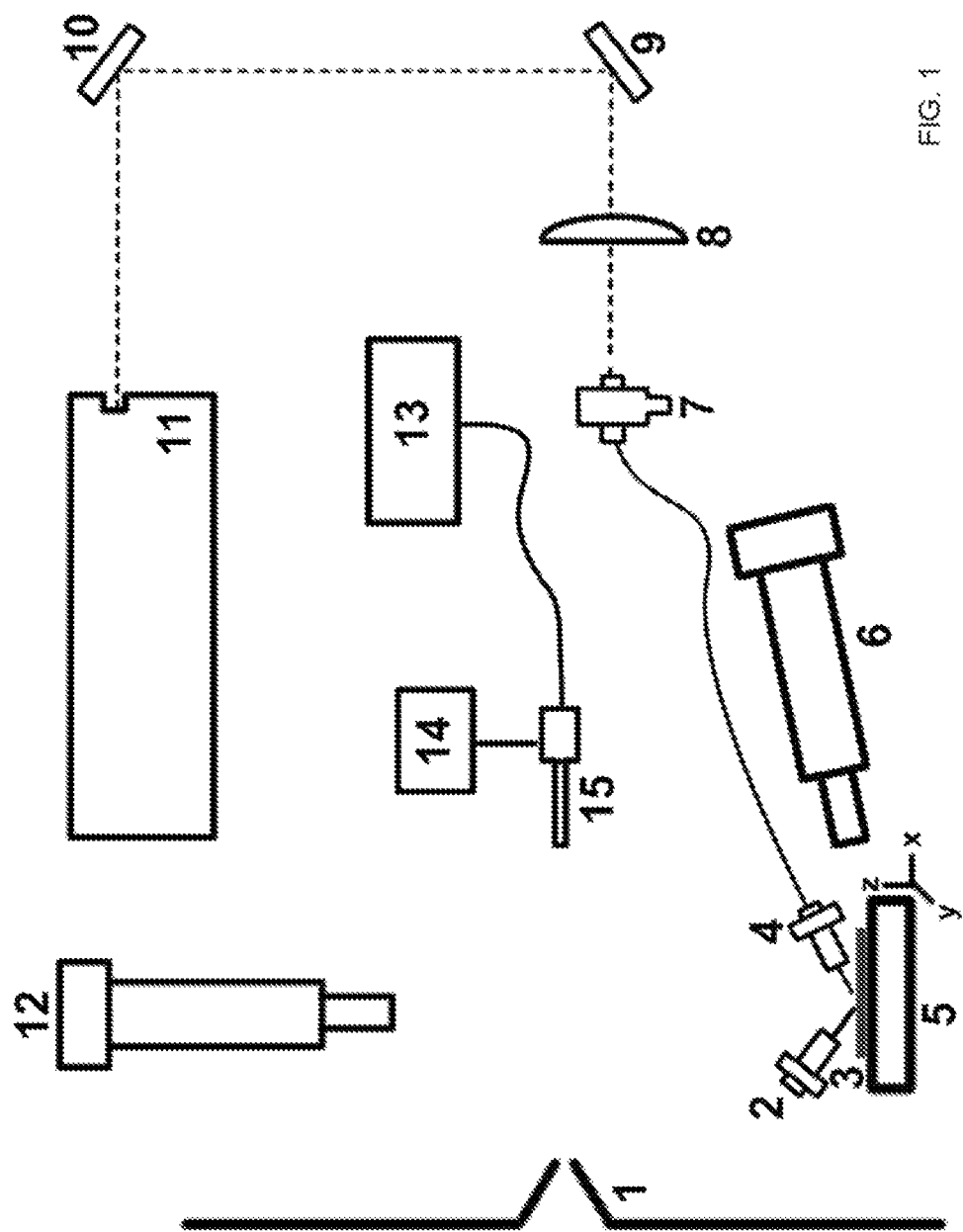
FIG. 1 includes an illustration of a LAESI-MS system according to various embodiments described herein.

As generally used herein, the articles "one", "a", "an" and "the" refer to "at least one" or "one or more", unless otherwise indicated.

As generally used herein, the terms "including" and "having" mean "comprising".

As used herein, the terms "LAESI-MS" refer to laser ablation electrospray ionization mass spectrometry.

As generally used herein, the term "about" refers to an acceptable degree of error for the quantity measured, given the nature or precision of the measurements. Typical exemplary degrees of error may be within 20%, 10%, or 5% of a given value or range of values. Alternatively, and particularly in biological systems, the terms "about" refers to values within an order of magnitude, potentially within 5-fold or 2-fold of a given value.

All numerical quantities stated herein are approximate unless stated otherwise; meaning that the term "about" may be inferred when not expressly stated. The numerical quantities disclosed herein are to be understood as not being strictly limited to the exact numerical values recited. Instead, unless stated otherwise, each numerical value is intended to mean both the recited value and a functionally equivalent range surrounding that value. At the very least, and not as an attempt to limit the application of the doctrine of equivalents to the scope of the claims, each numerical parameter should at least be construed in light of the number of reported significant digits and by applying ordinary rounding techniques. Notwithstanding the approximations of numerical quantities stated herein, the numerical quantities described in specific examples of actual measured values are reported as precisely as possible.

All numerical ranges stated herein include all sub-ranges subsumed therein. For example, a range of "1 to 10" is intended to include all sub-ranges between and including the recited minimum value of 1 and the recited maximum value of 10. Any maximum numerical limitation recited herein is intended to include all lower numerical limitations. Any minimum numerical limitation recited herein is intended to include all higher numerical limitations.

In the following description, certain details are set forth in order to provide a better understanding of various embodiments of ionization sources for mass spectrometers and methods for making and using the same. However, one skilled in the art will understand that the embodiments described herein may be practiced without these details. In other instances, well-known structures and methods associated with mass spectrometers and methods of mass spectrometry may not be shown or described in detail to avoid unnecessarily obscuring descriptions of the embodiments of this disclosure.

This disclosure describes various features, aspects, and advantages of various embodiments of ionization sources for mass spectrometers and methods for making and using the same. It is understood, however, that this disclosure embraces numerous alternative embodiments that may be accomplished by combining any of the various features, aspects, and advantages of the various embodiments described herein in any combination or sub-combination that one of ordinary skill in the art may find useful.

Eukaryotic cells may be found in animals, plants, and microorganisms. Eukaryotic cells may include a cell wall and/or a cell membrane, and subcellular components that may be enclosed within a membrane. The subcellular components may provide a specific function. Some examples of subcellular components include cytoplasm and organelles including, but not limited to, a nucleus, a mitochondrion, a chloroplast, a ribosome, an endoplasmic reticulum, a Golgi apparatus, a lysosome, a proteasome, a secretory vesicle, a vacuole, and a microsome. Some organelles, such as mitochondria and chloroplasts, may have their own genome separate from that found in the nucleus. Prokaryotic cells may be found in microorganisms, such as bacteria and archaea. Prokaryotic cells generally lack a nucleus, and may include a cell wall and/or a cell membrane and other subcellular components. Prokaryotic cells may include subcellular components lacking a membrane.

Analysis of subcellular components in single cells, such as the cytoplasm and organelles, may provide insight into the metabolism and/or metabolites of a living cell. Metabolism generally refers to the chemical processes of a living cell or organism that support and maintain life. The products of these chemical processes may be generally referred to as metabolites. The subcellular components may include metabolites related to their functions. The subcellular distribution of metabolites in the cell may change depending on its biological state, developmental stage, history, and/or environment. For example, the metabolic micro-compartmentalization and/or metabolic channeling may provide means for transporting metabolites and intermediates among active sites of subcellular components. When the metabolites exhibit locally restricted diffusion, the cell may show indicia of intracellular heterogeneity of metabolites and/or compartmentalization of metabolites in particular organelles and/or other subcellular components. Identification and analysis of metabolite distribution may facilitate a better understanding of cell function.

In certain embodiments, the sample may comprise a single cell, cells, small cell populations, cell lines, and/or tissues, each sample comprising water. The single cell may have a smallest dimension less than 100 micrometers, such as less than 50 μm, less than 25 μm, and/or less than 10 μm. The single cell may have a smallest dimension from 1 μm to 100 μm, such as from 5 μm to 50 μm, and from 10 μm to 25 μm. In at least one embodiment, the single cell may have a smallest dimension from 1 μm to 10 μm. The small cell population may comprise 10 cells to 1 million cells, such as 50 cells to 100,000 cells, and 100 cells to 1,000 cells. In various embodiments, the sample may comprise a high, native water concentration. In various embodiments, the sample may comprise a native water concentration. In various embodiments, the sample may comprise a dehydrated sample that is rehydrated. In various embodiments, the rehydrated sample may be rehydrated via an environmental chamber and/or an aqueous solution.

In various embodiments, the method may comprise a stable isotope exchange, such as, for example, a hydrogen/deuterium exchange. A cell may comprise a subcellular component comprising at least one exchangeable hydrogen. The at least one exchangeable hydrogen may comprise, for example, —OH, —NH$_2$, =NH, and/or —SH. In various embodiments, the method may comprise contacting an isotope exchange agent and the cell and/or tissue to exchange the at least one exchangeable hydrogen with at least one isotope. In various embodiments, the isotope exchange agent may comprise deuterium oxide (D$_2$O), or deuterated methanol. In various embodiments, the stable isotope may be incorporated in at least one component of the growth medium for cell cultures and/or tissue cultures. In various embodiments, the stable isotope may be incorporated in at least one component of the food supply of a living organism. Through the uptake of the stable isotope labeled molecule into the living organism, it may be metabolized by the organism. In various embodiments, the isotope may comprise, for example, one or more of $^2$H, $^{13}$C, $^{15}$N, $^{18}$O and $^{34}$S. In various embodiments, the sample may comprise a deuterated sample. Single cell or subcellular analysis of the cell or tissue samples by LAESI-MS may be performed after the stable isotope exposure.

Incorporation of the stable isotopes into the molecules of the cells may reveal transport and metabolism processes in the cell, tissue, or organism.

In various embodiments, microdissection and LAESI-MS may be utilized for in-situ identification and analysis of a cell and/or subcellular components. In various embodiments, microdissection of the cell may expose the cytoplasm and/or other subcellular components, such as, for example, the nucleus. The cytoplasm and other subcellular components may comprise one or more biomolecules, such as metabolites, lipids, lipid precursors, lipid components, nucleic acids, proteins, peptides, carbohydrates, and combinations thereof. The cytoplasm and/or other subcellular components may be subjected to LAESI-MS to detect indicia of the one or more biomolecules, such as, for example peaks in the mass spectra corresponding to the one or more biomolecules. In various embodiments, the relative intensity of the peaks may be compared to the relative intensities of other peaks and/or standard peaks for the one or more biomolecules.

Certain embodiments of the LAESI ionization sources for mass spectrometers and methods of making and using the same described herein may provide certain advantages over other approaches of mass spectrometric analysis. The advantages may include, but are not limited to, in situ analysis, in situ single cell analysis, in situ subcellular analysis, in vivo analysis, in vivo single cell analysis, in vivo subcellular analysis, simultaneous detection of multiple components in samples, independent optimization of ablation conditions and ionization conditions, a wider dynamic range of samples that may be used, quantitative analysis, semi-quantitative analysis, operation under ambient conditions, simpler sample preparation, minimal sample manipulation, minimal sample degradation, direct analysis of tissues and cells, analysis of large samples, two-dimensional mass spectrometric imaging at atmospheric pressure, three-dimensional mass spectrometric imaging at atmospheric pressure, the ability to monitor environmental effects on multiple cells, single cells, or subcellular components, improved sampling time, positional sensitivity, improved sensitivity to surface properties, and/or improved detection limits.

In various embodiments, a method of in situ analysis of a cell having a native water concentration may generally comprise micro-dissecting the cell to expose at least one subcellular component therein comprising at least one chemical species of interest, subjecting the at least one subcellular component to laser ablation electrospray ionization mass spectrometry, and determining, by laser ablation electrospray ionization mass spectrometry, a relative intensity of a signal of the chemical species. In various embodiments, the chemical species of interest may be a biomolecule, such as, for example a metabolite.

According to certain embodiments, a method of subcellular LAESI-MS may generally comprise micro-dissecting a cell to expose at least one subcellular component therein and subjecting the at least one subcellular component to LAESI-MS. In various embodiments, the method may comprise staining the cell to enhance the visibility of cell walls, cell membranes, and/or subcellular components. In various embodiments, micro-dissecting the cell may expose the cytoplasm and at least one organelle therein. In various embodiments, micro-dissecting the cell may comprise one or more of piercing, cutting, rupturing, separating and removing at least a portion of the cell wall and/or cell membrane by a microdissection tool, an optical tweezer, and/or at least one laser pulse. In various embodiments, micro-dissecting the cell may comprise one or more of cutting, piercing, rupturing and removing at least a portion of the membrane of the subcellular component therein by a microdissection tool, an optical tweezer, and/or at least one laser pulse. In various embodiments, micro-dissecting the cell may expose the cytoplasm and at least one organelle therein such that the cytoplasm and at least one organelle therein are visible. In various embodiments, micro-dissecting the cell may expose the cytoplasm and at least one organelle therein such that the cytoplasm and at least one organelle therein are accessible to a laser pulse. In various embodiments, a microscope, such as a long distance video microscope or an inverted microscope, may be used to visualize the microdissection to reduce and/or eliminate damage to any surrounding cells and/or subcellular components.

In various embodiments, micro-dissecting the cell may comprise cutting at least a portion of the cell wall and/or cell membrane by at least one laser pulse. The laser pulse may have a wavelength of 100 nm to 8 µm, a diameter of 0.5-20 µm, a pulse length of less than one picosecond to 100 ns, and a repetition rate of up to 100 MHz, such as, for example, 0.1 Hz to 100 MHz, under ambient conditions. In various embodiments, the laser pulse may have a wavelength of 100 nm to 400 nm, such as 300 nm. In various embodiments, the laser pulse may have a wavelength of 700 nm to 3000 nm, 2000 nm to 4000 nm, such as, for example, 800 nm and 2940 nm. In various embodiments, the laser pulse may have a wavelength of 2 µm to 4 µm, such as, for example, about 3 µm. In various embodiments, the laser pulse may have a diameter of 0.5 µm to 1 µm, 1 µm to 20 µm, and 1 µm to 5 µm. In various embodiments, the laser pulse may have a pulse length of 200 fs to 10 ns, 1 ns to 100 ns, and 1 ns to 5 ns. In various embodiments, the laser pulse may have a repetition rate up to 100 Hz, such as, for example, 0.1 Hz to 100 Hz. In at least one embodiment, the laser pulse may have a wavelength of 800 nm, a diameter of 1 µm, and a pulse length of 200 fs. In at least one embodiment, the laser pulse may have a wavelength of 100 nm to 400 nm, a diameter of 1 µm to 5 µm, and a pulse length of 1 ns to 100 ns. In at least one embodiment, the laser pulse may have a wavelength of 2940 nm, a diameter of 1 to 20 µm, and a pulse length of 5 ns.

In various embodiments, a laser system to generate the least one laser pulse for microdissection may comprise a laser and a focusing system. The laser may be selected from the group consisting of a UV laser and an infrared laser, such as, for example, a mid-infrared laser. The UV laser may include, but not limited to, an excimer laser, a frequency tripled Nd:YAG laser, a frequency quadrupled Nd:YAG laser, and a dye laser. The infrared laser may include, but not limited to, a carbon dioxide laser, a Nd:YAG laser, and a titanium-sapphire laser. The mid-infrared laser may include, but not limited to, an Er:YAG laser and a Nd:YAG laser driven optical parametric oscillator (OPO). In various embodiments, the laser system may comprise a tunable titanium-sapphire mode-locked laser to generate laser pulses having a 800 nm wavelength, a 1 µm diameter, 200 fs pulse length, 76 MHz repetition rate, and 5 nJ energy per pulse. In various embodiments, the laser system may comprise a tunable titanium-sapphire mode-locked laser and a regenerative amplifier associated with the titanium-sapphire laser to generate laser pulses having a 800 nm wavelength, 200 fs pulse length, 1 kHz repetition rate, and 1 mJ energy per pulse. A tunable titanium-sapphire mode-locked laser is commercially available from Coherent (Santa Clara, Calif.) under the trade designation Mira 900. A regenerative amplifier is commercially available from Positive Light (Los Gatos, Calif.) under the trade designation Spitfire.

Figure 2:
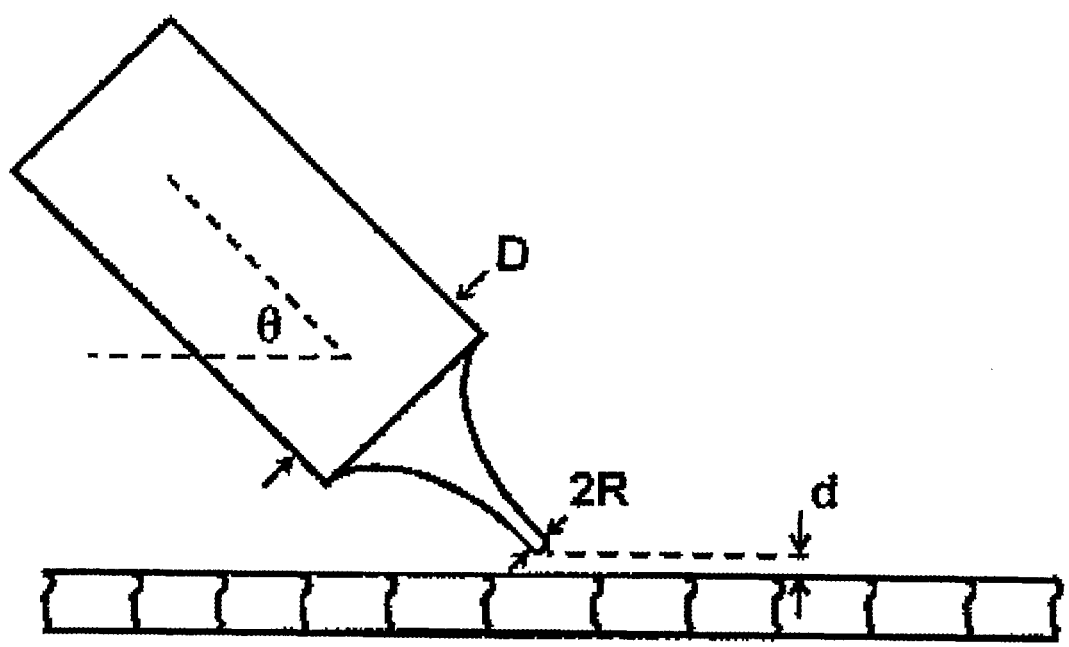
FIG. 2 includes an illustration of a sharpened optical fiber tip positioned above a sample according to various embodiments described herein. The optical fiber core diameter, D, the etched tip radius of curvature, R, the angle of inclination, θ, and the distance from the sample surface, d, are shown.

In various embodiments, the focusing system may comprise a mirror, a prism, a coupling lens, a focusing lens, and/or an optical fiber. In at least one embodiment, a plano-convex focusing lens having a 50 mm focal length may be used to focus the laser beam. In at least one embodiment, a planoconvex calcium fluoride lens having a 50 mm focal length may be used to couple the laser energy to a germanium oxide optical fiber having a 450 μm core diameter. The focusing system may comprise single element lenses, aspherical lenses, composite lenses, microscope objective lenses, and reflective microscope objective lenses. In various embodiments, the focusing system may comprise an optical fiber having a core diameter (D), a tip radius of curvature (R), a tip angle of inclination (θ), and a tip distance from the cell (d). Referring to FIG. 2, in various embodiments, the microdissection optical fiber core diameter D may be 15-450 μm, such as 450 μm, the microdissection optical fiber tip radius of curvature R may be 0.1 μm to 25 μm, such as, for example, 0.25 μm to 5 μm and 7.5 to 12.5 μm, the microdissection optical fiber tip angle of inclination θ may be 15-90°, such as 35-55°, and the microdissection optical fiber tip distance d may be 0-50 μm, such as 0-10 μm and 0-30 μm.

In various embodiments, micro-dissecting the cell may comprise cutting at least a portion of the cell and/or transporting subcellular components by an optical tweezer. In various embodiments, the optical tweezer system may comprise a laser, a beam expander comprising two or more lenses, beam steering optics comprising one or more of a mirror, a lens, a high numerical aperture objective lens, and a condenser. Optical tweezer systems may be generally described in J. R. Moffitt et al., Annu. Rev. Biochem. 2008.77:205-228, which is hereby incorporated herein by reference in its entirety.

In various embodiments, micro-dissecting the cell may comprise cutting at least a portion of the cell wall and/or cell membrane by a microdissection tool selected from the group consisting of a needle, a pin, and a hook. In various embodiments, the microdissection tool may have a tip diameter of 0.5 μm to 30 μm. In various embodiments, the microdissection tool may comprise a metal microdissection tool and/or a glass microdissection tool. In various embodiments, the metal may comprise tungsten, iron, and/or an alloy, such as, for example, stainless steel. In various embodiments, the microdissection tool may comprise a metal needle having a tip diameter of 0.5 μm to 30 μm, such as, for example, 1 μm to 5 μm. In various embodiments, the microdissection tool may comprise a silica, quartz, or glass needle or capillary having a tip diameter of 0.5 μm to 30 μm. The glass needle may comprise a pulled or micro-fabricated microinjection capillary. The pulled or micro-fabricated microinjection capillary may comprise a pulled or micro-fabricated borosilicate glass micropipette. Silica tips are commercially available from New Objective, Inc. (Woburn, Mass.) under the trade designation SilicaTips and TaperTips.

In various embodiments, the microdissection tool may comprise a tungsten needle having a tip diameter of 1 μm to 5 μm. Microdissection tools, such as a tungsten microdissecting needles, having a 1 μm tip diameter are commercially available from Roboz Surgical Instrument Co., (Gaithersburg, Md.), and microdissecting needles having a 5 μm tip diameter are commercially available from Harvard Apparatus, (Holliston, Mass.). The microdissecting needle may be placed in a microdissecting needle holder (RS6060 or RS6061, Roboz Surgical Instrument Co., Gaithersburg, Md.) attached to a micromanipulator (MN-151, Narishige, Tokyo, Japan). The actuators of the micromanipulator for the needle may have a course adjustment range of 25 mm in the X and Y axis and 20 mm in the Z axis and a minimum graduation of 5 μm. In various embodiments, the microdissection tool may be positioned proximate to a sample at a zenith angle of 0-90°, such as, for example, 10-90° and 45°, until the sample surface is pierced. The sample surface may be cut and/or separated from the remaining sample using the fine adjustment of the micromanipulator to expose the subcellular components therein.

In various embodiments, the microdissection tool may comprise a piezo electrically-driven microdissection tool. The piezo electrically-driven microdissection tool may comprise a microdissection tool, a microdissection tool holder, a controller, a piezomicromanipulator drive unit and an operation box. A piezo electric drive unit is commercially available from Prime Tech Ltd. (Tsukuba, Ibaraki-ken, Japan) under the trade designation Piezo Micromanipulator/Piezo Impact Drive Unit. The microdissection tool may be connected to a piezo micromanipulator drive unit. In various embodiments, a portion of the microdissection tool may be positioned within a microdissection tool holder connected to a piezo micromanipulator drive unit. The piezo micromanipulator drive unit may have a moving range of 5 mm, a traveling speed of 0-0.04 mm/s, and a traveling resolution of 0.1 μm. The piezo micromanipulator drive unit may utilize a piezoelectric effect to advance, in a highly controlled, rapid manner, the tip of the microdissection tool a short distance, such as, for example, up to 20 μm and 0.5-20 μm at a high forward velocity, such as, for example, 100 mm/s, and a reverse velocity, such as, for example, 50 mm/s. The intensity and interval between each pulse may be varied and regulated by an operation box. For example, the operation box may have various speed levels and various intensity levels. The piezo micromanipulator drive unit may vibrate the microdissection tool along its axis with ultrasound frequencies. The piezo pulses may be applied to the microdissection tool to microdissect the sample. The piezo pulses may be applied to the microdissection tool to pierce, cut, rupture, separate and/or remove at least a portion of the cell wall and/or cell membrane. For example, the vibrating microdissection tool may pierce the cell wall and the cell membrane.

Figure 3A:
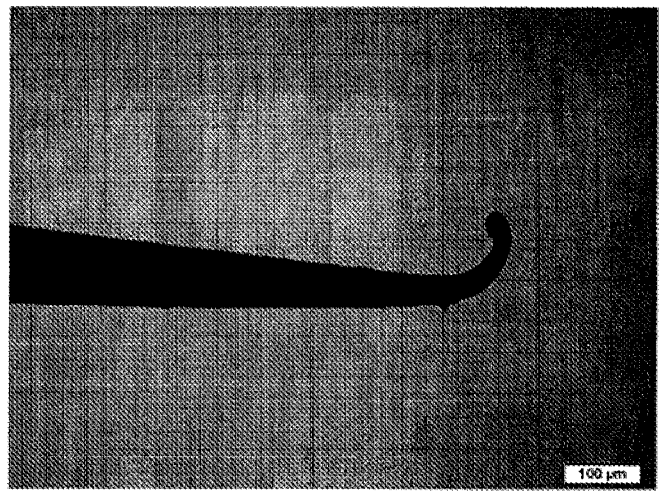
FIGS. 3A-C include microscope images of a tungsten microdissection tool.
Figure 3B:
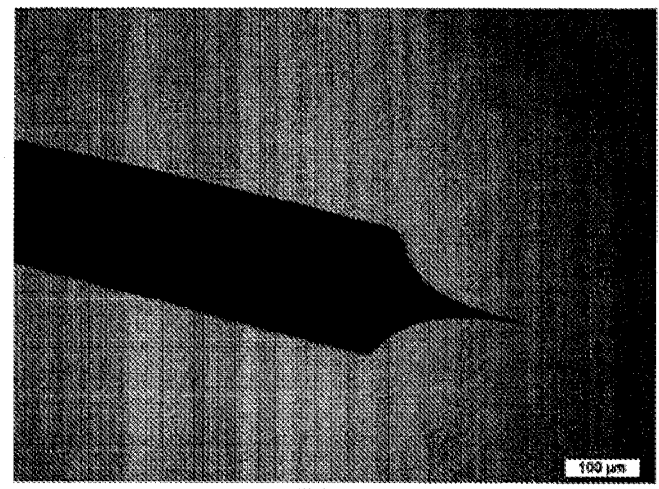
Figure 3C:
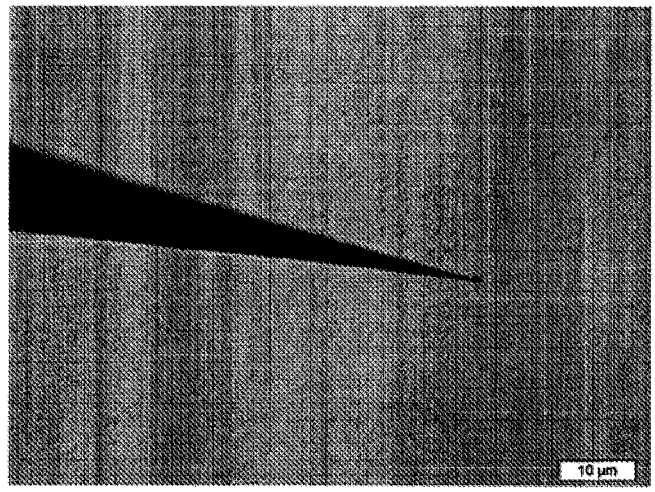

In various embodiments, the method may comprise sharpening the microdissection tool. For example, a microdissecting needle may be electrochemically etched when the tip becomes blunt and/or when the tip is unable to pierce the cell. For example, a microdissecting needle may be placed in a 1 M to 3 M NaOH electrolyte solution, and used as a positive electrode. A power supply may provide about 3 V to the electrolyte solution to generate a sharper tip via the drop-off method. During drop-off method, the portion of the microdissecting needle positioned in the electrolyte solution may pinch off and drop into the electrolyte solution generating a shaper tip. The sharper tip may, for example, have a 0.5 μm to 5 μm diameter. FIGS. 3A-C include images of a tungsten microdissecting needle before etching (FIG. 3A) and after etching (FIGS. 3B and C). As shown in FIGS. 3B and 3C, the tip of the microdissecting needle after etching may be 600 nm.

According to certain embodiments, the sample may be placed on a sample mount, such as a glass slide. A long distance video microscope may be used to visualize the sample during microdissection. For example, the long distance video microscope may be a 7× precision zoom optic (Edmund Optics, Barrington, N.J.), a 2× infinity-corrected objective lens (M Plan Apo 2×, Mitutoyo Co., Kanagawa, Japan), and a CCD camera (Marlin F131, Allied Vision Technologies, Stadtroda, Germany) may be placed orthogonal to the sample. In various embodiments, the sample may be stained to improve the visibility of the subcellular components. The stain may include, but not limited to, toluidine blue, hematoxylin-eosin, methylene blue chloride, or aniline fuchsin and/or methyl green. For example, the sample may be immersed in a solution of 0.05% toluidine blue in distilled water for one minute, rinsed with distilled water, and then mounted onto a precleaned glass slide.

According to certain embodiments, a LAESI-MS system may generally comprise a laser system, an electrospray apparatus, and a mass spectrometer. The laser system may comprise a laser, a focusing system comprising optical fibers, coupling lenses, and/or focusing lenses, and an x-y-z translation stage having a sample mount. The laser may include, but not limited to, an Er:YAG laser, a Nd:YAG laser driven optical parametric oscillator (OPO), and a free electron laser. The electrospray apparatus may comprise an electrospray ionization emitter having a power supply and a syringe pump. The mass spectrometric ion source may comprise an environmental chamber or a shroud to enclose the sample, the sample holder, and/or the electrospray emitter. The translation stage and the sample environment may be temperature controlled and/or atmosphere controlled to maintain sample integrity and/or avoid condensation of moisture from the environment. The atmosphere may comprise ambient atmosphere. The temperature may ranges from −10° C. to 60° C. The relative humidity may range from 10% to 90%. The pressure may range from more than atmospheric pressure to less than vacuum.

Referring to FIG. 1, in certain embodiments, a LAESI-MS system may generally comprise a first long distance microscope 12 to visualize a top view of the sample 3 positioned on a three-axis translation stage 5 to assist the microdissection and aiming of the optical fiber tip 4 and a second long distance microscope 6 to visualize the side view of the sample 3 to assist controlling the distance between the optical fiber tip 4 and the sample 3. A micromanipulator including a microdissection tool 2, such as, for example, a micro-needle, may be used for micro-dissecting the sample 3. The electrospray may be produced by a high voltage power supply 14 applying voltage to the electrospray capillary emitter 15 and maintaining a constant solution flow rate by a syringe pump 13. The laser pulses from the mid-infrared laser 11 may be coupled to an optical fiber tip 4 via a fiber mount 7, mirrors 9, 10, and a $CaF_2$ focusing lens 8. The ablation plume generated by applying the laser pulse via the optical fiber tip 4 to the sample 3 may be intercepted by the electrospray plume and post-ionized to form ions analyzed and detected by the mass spectrometer 1. The three-axis translation stage 5 may comprise a three-axis translation stage with temperature control.

In certain embodiments, the laser may comprise an infrared laser. The infrared laser may operate at a wavelength from 2600 nm to 3450 nm, such as 2800 nm to 3200 nm, and 2930 nm to 2950 nm. The laser may comprise a mid-infrared pulsed laser operating at a wavelength from 2600 nm to 3450 nm, a repetition rate from 1 Hz to 100 Hz, and a pulse width from 0.5 ns to 100 ns. In at least one embodiment, the laser may comprise a diode pumped Nd:YAG laser-driven optical parametric oscillator (OPO) (Vibrant IR, Opotek, Carlsbad, Calif.) operating at 2940 nm, 100 Hz repetition rate, and 5 ns pulse width. The optical fiber may comprise a germanium oxide ($GeO_2$)-based glass optical fiber (450 µm core diameter, HP Fiber, Infrared Fiber Systems, Inc., Silver Spring, Md.) and the laser pulse is coupled into the fiber by a plano-convex $CaF_2$ lens (Infrared Optical Products, Farmingdale, N.Y.). A high-performance optical shutter (SR470, Stanford Reseach Systems, Inc., Sunnyvale, Calif.) may be used to select the laser pulses. One end of the optical fiber may be held by a bare fiber chuck (BFC300, Siskiyou Corporation, Grants Pass, Oreg.) attached to a micromanipulator (NMN-21, Narishige, Tokyo, Japan). The other end of the optical fiber may be etched in a 1% $HNO_3$ solution to generate a tip radius of curvature from 1 µm to 50 µm, such as 5 µm to 25 µm, and 10 µm to 15 µm. In at least one embodiment, the radius of curvature may be 10 µm. The optical fiber may deliver the laser pulse to the sample. The energy of a laser pulse before coupling into the optical fiber may be from 0.1 mJ to 6 mJ, and the pulse-to-pulse energy stability generally corresponds to 2% to 10%. In at least one embodiment, the energy of a laser pulse before coupling into the optical fiber may be 554±26 µJ, thus the pulse-to-pulse energy stability corresponds to 5%. The laser system may be operated at 100 Hz from 0.01 seconds to 20 seconds to ablate a sample. In at least one embodiment, laser system may be operated at 100 Hz for 1 second to ablate a sample. In certain embodiments, 1 to 100 laser pulses may be delivered to a sample to ablate the sample.

In certain embodiments, the electrospray source may comprise a low noise syringe pump (Physio 22, Harvard Apparatus, Holliston, Mass.) to supply the electrospray solution to a tapered stainless steel emitter (inner diameter 50 µm, MT320-50-5-5, New Objective, Woburn, Mass.). The low noise syringe pump may supply the electrospray solution at a rate from 10 nL/min to 10 µL/min. In at least one embodiment, the low noise syringe pump may supply the electrospray solution at 300 nL/min. The aqueous electrospray solution may comprise at least one of 50% (v/v) methanol with 0.1% (v/v) acetic acid, 50% (v/v) methanol with 0.1% (v/v) formic acid, 50% (v/v) methanol with 0.1% (v/v) trifluoroacetic acid, 50% (v/v) methanol with 0.1% (v/v) ammonium acetate. In at least one embodiment, the electrospray solution may comprise 50% (v/v) aqueous methanol solution with 0.1% (v/v) acetic acid. The tapered stainless steel emitter may have an outside diameter from 100 µm to 500 µm and an insider diameter from 10 µm to 200 µm. The power supply may comprise a regulated power supply (PS350, Stanford Research Systems, Sunnyvale, Calif.), to provide a stable high voltage from 2.5 to 5 kV to the electrospray emitter to generate the electrospray. In at least one embodiment, the regulated power supply may provide a 3.0 kV to the electrospray emitter. The electrospray emitter may be mounted on a manual translation stage to optimize the LAESI signal by adjusting the relative position of the sample, electrospray emitter, and/or inlet orifice of the mass spectrometer. The electrospray solution may be applied at an angle from 0° to 90°, such as 30°, 45°, and 60°, into the ablation plume. The angle may be adjusted from 0° to 90° to optimize ion production. In at least one embodiment, the electrospray solution may be applied at a right angle) (90° into the ablation plume.

According to certain embodiments, the mass spectrometer orifice may be on the same or a different axis as the electrospray emitter of the LAESI ion source. The angle between the mass spectrometer orifice and electrospray emitter of the LAESI ion source may be from 0° to 90°, such as 30°, 45°, and 60°. The distance from the mass spectrometer orifice to the electrospray emitter tip may be from 1 mm to 20 mm, such as 5 mm to 15 mm. In at least one embodiment, the distance from the mass spectrometer orifice to the electrospray emitter tip may be 12 mm. The sample may be placed onto a precleaned microscope glass slide (catalog no. 125496, Fisher Scientific, Pittsburgh, Pa.). The sample may be placed onto a stepper motor-driven three axis precision flexure stage (NanoMax TS, Thorlabs, Newton, N.J.). The sample may be 1 mm to 30 mm below the spray axis, such as 5 mm to 25 mm, and 10 mm to 20 mm. In at least one embodiment, the sample may be 15 mm below the spray axis. In one experiment, no ions were detected by the mass spectrometer when the ESI was off, indicating that no ions directly induced by the laser were collected.

The ions produced by the LAESI ion source may be analyzed by a mass spectrometer. The mass spectrometer may comprise an orthogonal acceleration time-of-flight mass spectrometer (Q-TOF Premier, Waters Co., MA). The orifice of the mass spectrometer may have an inner diameter from 100 µm to 500 µm, such as 225 µm to 375 µm. In at least one embodiment, the orifice of the mass spectrometer may have an inner diameter from 100 µm to 200 µm, such as 127 µm. The orifice of the mass spectrometer may be extended by a straight or curved extension tube having a similar inner diameter as the orifice of the mass spectrometer and a length from 20 mm to 500 mm. The interface block temperature may be from ambient temperature to 150° C., such as 23° C. to 90° C., and 60° C. to 80° C. In at least one embodiment, the interface block temperature may be 80° C. The potential may be from −100 V to 100 V, such as −70 V to 70 V. In at least one embodiment, the potential may be −70 V. Tandem mass spectra may be obtained by collision activated dissociation (CAD) with a collision gas, such as argon, helium or nitrogen, at a collision cell pressure from $10^{-6}$ mbar to $10^{-2}$ mbar, and with collision energies from 10 eV to 200 eV. In at least one embodiment, the collision gas may be argon, the collision cell pressure may be $4 \times 10^{-3}$ mbar, and the collision energies may be from 10 eV to 25 eV.

In certain embodiments, the laser pulse may be steered by gold-coated mirrors (PF10-03-M01, Thorlabs, Newton, N.J.) and coupled into the cleaved end of the optical fiber by a plano-convex calcium fluoride lens (Infrared Optical Products, Farmingdale, N.Y.) having a focal length from 2 mm to 100 mm, such as 25 mm to 75 mm, and 40 mm to 60 mm. In at least one embodiment, the focal length may be 50 mm. The optical fiber may be held by a bare fiber chuck (BFC300, Siskiyou Corporation, Grants Pass, Oreg.). The optical fiber may be positioned by a five-axis translator (BFT-5, Siskiyou Corporation, Grants Pass, Oreg.).

In certain embodiments, the optical fiber may comprise at least one of a $GeO_2$-based glass fiber, a fluoride glass fiber, and a chalcogenide fiber. The optical fiber may have a high laser-damage threshold due to its high glass transition temperature. The Hytrel and polyimide coatings may be stripped off both ends of the fiber by the application of 1-methyl-2-pyrrolidinone (at 130° C. to 150° C. for 1 min). After stripping off the Hytrel and the polyimide coatings, the fiber ends may be cleaved with a Sapphire blade (KITCO Fiber Optics, Virginia Beach, Va.) by scoring and gently snapping them. Chemical etching of the $GeO_2$-based glass fiber tip may be achieved by dipping one of the cleaved fiber ends 0.5 mm deep into 24° C. 1% $HNO_3$ solution in a wide beaker to provide a low meniscus curvature. The meniscus formed at the fiber end may gradually etch the 450 µm diameter core into a sharp tip having a radius of curvature (R) of 15 µm. Prior to use, the etched tips may be washed with deionized water. In certain embodiments, no visible change of the fiber tip may be observed after performing the LAESI technique which may indicate the absence of damage or contamination.

In certain embodiments, the etched end of the fiber may be attached to a micromanipulator (MN-151, Narishige, Tokyo, Japan) to move the etched end of the fiber closer to the sample. The distance from the etched end of the fiber and the sample may be from contact (0 µm) to 50 µm. In at least one embodiment, the coordinate system may be aligned so that the x-y plane coincides with the sample and the x-axis is parallel with the emitter, the optical fiber is positioned at an azimuth angle from 20° to 160° and a zenith angle from 20° to 70°. In at least one embodiment, the azimuth angle may be 135° and the zenith angle may be 45°. The zenith angle of 45° may provide an acceptable trade-off between the shape of the ablation mark and signal intensity reduction by blocking the expanding plume. A thin sample material deposit may be observed on the fiber tip after ablation. In these cases, the fiber may be retracted from the surface and elevated laser pulse energy may be used to clean the tip. In at least one embodiment, the distance between the fiber tip and the sample surface (h) may be twice the tip radius of curvature, 2 R. This may result in an ablation mark with an average diameter of 2.5 R. In at least one embodiment, the distance between the fiber tip and the sample surface may be 30 µm, resulting in an ablation mark with an average diameter of 37 µm. Microscope images of the ablation marks may be obtained by an upright microscope (BX 51, Olympus America Inc., Center Valley, Pa.) in either reflected or transmitted mode and by an inverted microscope.

In certain embodiments, the LAESI system may comprise a visualization system. The distance between the fiber tip and sample surface may be monitored by a long distance video microscope (InFocus Model KC, Infinity, Boulder Colo.) with a 5× infinity corrected objective lens (M Plan Apo 5×, Mitutoyo Co., Kanagawa, Japan), and the image may be captured by a CCD camera (Marlin F131, Allied Vision Technologies, Stadtroda, Germany). With the environmental vibration in the low micrometer range, an approximate distance from 30 µm to 40 µm may be maintained between the tip and the sample. A similar video microscope system may be used at a right angle to the sample surface to align the fiber tip over the location of interest in the sample for ablation. The visualization system may comprise a 7× precision zoom optic (Edmund Optics, Barrington, N.J.), fitted with a 5× infinity-corrected long working distance objective lens (M Plan Apo 5×, Mitutoyo Co., Kanagawa, Japan) or a 10× infinity-corrected long working distance objective lens (M Plan Apo 10×, Mitutoyo Co., Kanagawa, Japan) and a CCD camera (Marlin F131, Allied Vision Technologies, Stadtroda, Germany).

EXAMPLES

The various embodiments described herein may be better understood when read in conjunction with the following representative examples. The following examples are included for purposes of illustration and not limitation.

HPLC grade water and methanol, acetic acid, and 1-methyl-2-pyrrolidinone were purchased from Sigma-Aldrich (St. Louis, Mo.). Toluidine blue 1% aqueous solution was purchased from Home Training Tools, Ltd. (Billings, Mont.).

Figure 4A:
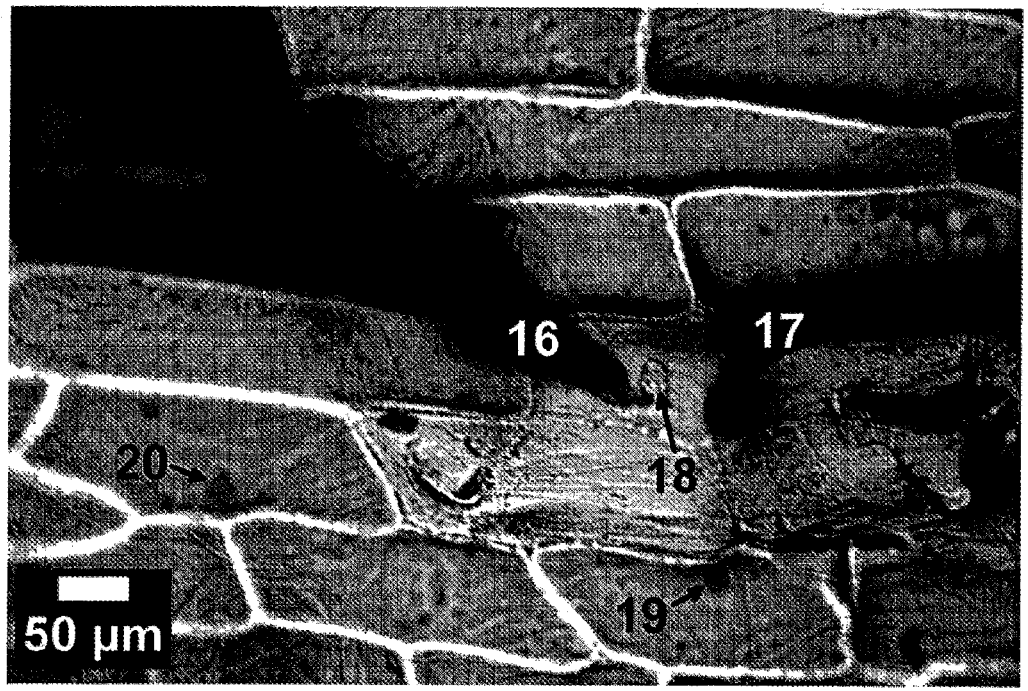
FIGS. 4A-C include microscope images of a dissected *Allium cepa* epidermal cell according to various embodiments described herein.

According to certain embodiments, the sample comprised *Allium cepa* (*A. cepa*) bulbs purchased from Washington, D.C. The *A. cepa* bulbs were stored at 4° C. prior to the analysis. A monolayer of the epidermal tissue of the *A. cepa* bulb was removed from the intact parenchyma tissue. Optionally, the removed epidermis was stained with toluidine blue to improve the visibility of the subcellular components. For example, the epidermis may be stained with toluidine blue to improve the visibility of nuclei. The wet surface of the epidermis may be immersed in a solution of 0.05% toluidine blue in distilled water for one minute. The stained epidermis may be rinsed with distilled water. A microscope image of the stained epidermal cells in the skin of the *A. cepa* bulb is shown in FIG. 4A. The sample may be placed on a precleaned glass slide about 10-15 mm below the spray axis.

To visualize the sample during microdissection, a video microscope having a 7× precision zoom optic (Edmund Optics, Barrington, N.J.), a 2× infinity-corrected objective lens (M Plan Apo 2×, Mitutoyo Co., Kanagawa, Japan), and a CCD camera (Marlin F131, Allied Vision Technologies, Stadtroda, Germany) was placed orthogonal to the sample.

Tungsten microdissecting needles having a 1 μm tip diameter (RS-6065, Roboz Surgical Instrument Co., Gaithersburg, Md.) or 5 μm tip diameter (72-0424, Harvard Apparatus, Holliston, Mass.) were placed in a microdissecting needle holder (RS6060 or RS6061, Roboz Surgical Instrument Co., Gaithersburg, Md.) associated with a micromanipulator (MN-151, Narishige, Tokyo, Japan). The actuators of the micromanipulator had a course adjustment range of 25 mm in the X and Y axis and 20 mm in the Z axis and a minimum graduation of 5 μm.

Figure 4B:
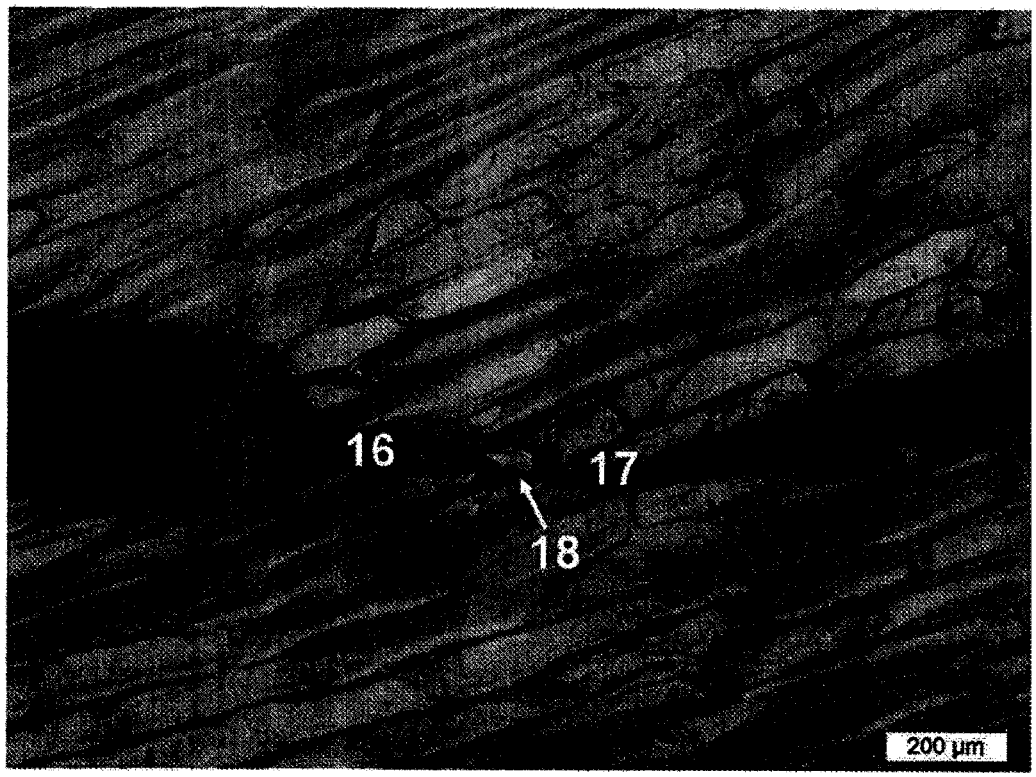
Figure 4C:
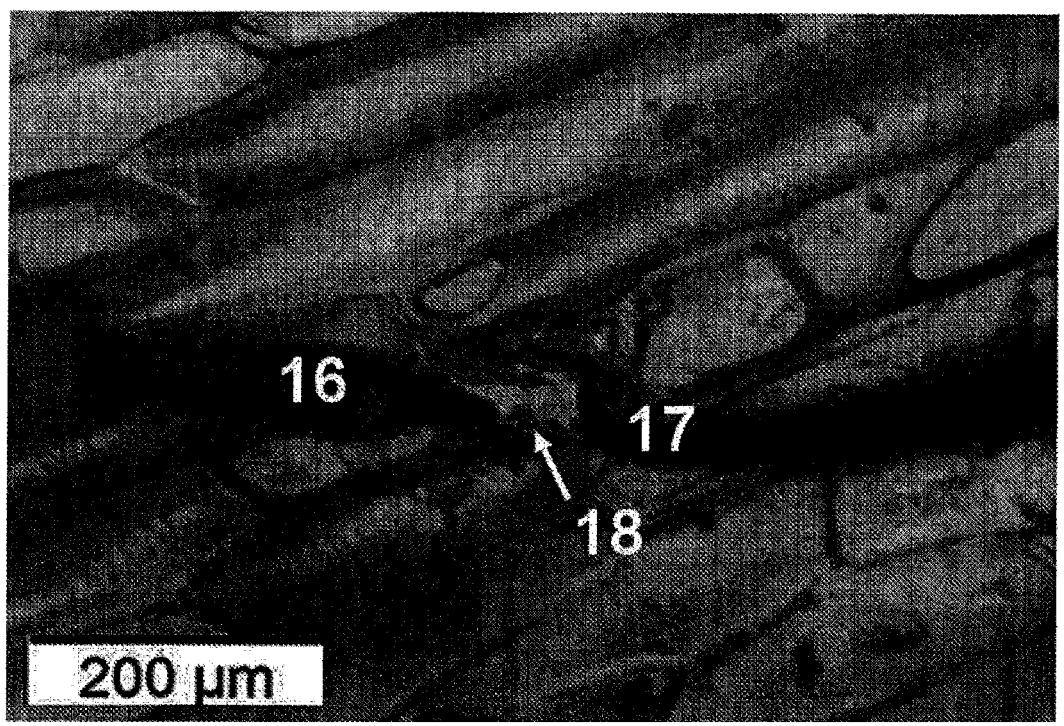

The needle was slowly lowered in the proximity of the outer edge of a single cell at a zenith angle of about 45° until the cell wall was pierced. The cell wall was cut along the inner edge and peeled back using the fine adjustment of the micromanipulator to expose the organelles and other subcellular components. As shown in FIG. 4A, the tip of the microdissecting needle 17 was used to pierce and cut the cell wall of a single *A. cepa* cell. The microdissecting needle 17 was used to separate the cell wall and cell membrane from the nucleus 18 to expose the nucleus 18. No or minimal damage to the surrounding cells was observed during microdissection. Undisturbed nuclei 19, 20 are shown in intact neighboring cells. Immediately after microdissection, the microdissecting needle 17 was retracted and the optical fiber 16 was aligned with the exposed subcellular component, such as the nucleus. As shown in FIGS. 4B and 4C, an etched optical fiber tip 16 may be positioned near the dissected cell to deliver at least one laser pulse to the nucleus 18 for LAESI-MS.

According to certain embodiments, the method of LAESI mass spectrometry was performed using a mid-infrared laser system. An optical parametric oscillator (OPO) (Vibrant IR or Opolette 100, Opotek, Carlsbad, Calif.) converted the output of a 100 Hz repetition rate Nd:YAG laser to mid-infrared laser pulses of 5 ns pulse width at 2940 nm wavelength. Individual laser pulses were selected using a high performance optical shutter (SR470, Standford Research Systems, Inc., Sunnyvale, Calif.). Beam steering and focusing was accomplished by gold coated mirrors (PF10-03-M01, Thorlabs, Newton, N.J.). For the ablation of tissue using conventional mass spectrometry having a laser spot size of 300 μm diameter, the laser pulse was focused by a single 75 mm focal length plano-convex antireflection-coated ZnSe lens or a 150 mm focal length plano-convex $CaF_2$ lens (Infrared Optical Products, Farmingdale, N.Y.). For ablation of a single cell and its subcellular components, the mid-infrared laser pulse was applied to the sample by a sharpened germanium oxide ($GeO_2$) optical fiber have a core diameter of 450 μm (HP Fiber, Infrared Fiber Systems, Inc., Silver Spring, Md.). A 50 mm focal length plano-convex $CaF_2$ lens (Infrared Optical Products, Farmingdale, N.Y.) was used to focus the laser pulse onto the distal end of the optical fiber.

The other end of the optical fiber was chemically etched in 1% $HNO_3$ solution to generate a tip radius of curvature of 15-50 μm, 15-25 μm, and 15 μm. To obtain a tip having 15 μm radius of curvature, for example, the end of the fiber was vertically lowered about 300 μm into the etchant. After 15 minutes, the generated tip spontaneously detached from the etchant surface. To obtain a tip having a 50 μm radius of curvature, for example, the end of the fiber was vertically lowered about 1.5 mm into the etchant. After 20 minutes, the tip was removed from the etchant before the tip spontaneously detached from the etchant surface. The tip was rinsed with deionized water to remove any residue of the etchant.

The optical fiber was held in a bare fiber chuck (BFC300, Siskiyou Corp., Grant Pass, Oreg.) that was attached to a micromanipulator (MN-151 or NMN-21, Narishige, Tokyo Japan). The optical fiber was positioned in close proximity to the sample at an inclination angle of about 45°. The optical fiber was aligned at an angle of 90° to the needle. The tip was monitored by a first video microscope positioned orthogonal to the sample. The distance between the tip and the sample surface was monitored by a second video microscope with a 7× precision zoom optic (Edmund Optics, Barrington, N.J.), a 5× infinity-corrected objective lens (M Plan Apo 5×, Mitutoyo Co., Kanagawa, Japan), and a CCD camera (Marlin F131, Allied Vision Technologies, Stadtroda, Germany) positioned at about 20° angle to the sample surface. The distance between the tip and the sample surface was about 30 μm.

According to certain embodiments, the electrospray system comprised a low-noise syringe pump (Physio 22, Harvard Apparatus, Holliston, Mass.) to feed a 50% (v/v) aqueous methanol solution containing 0.1% (v/v) acetic acid at 200-300 nL/min flow rate through a stainless steel emitter with tapered tip having an outside diameter of 320 μm and an inside diameter of 50 μm. (MT320-50-5-5, New Objective Inc., Woburn, Mass.). Stable high voltage (2800 V) was generated by a regulated power supply (PS350, Stanford Research Systems, Inc., Sunnyvale, Calif.). The regulated power supply provided 3,000 V directly to the emitter. The orifice of the sampling cone was on-axis with the electrospray emitter at a distance of 12 mm from its tip.

An orthogonal acceleration time-of-flight mass spectrometer (Q-TOF Premier, Waters Co., Milford, Mass.) having a mass resolution of 8,000 (FWHM) collected and analyzed the ions generated by the LAESI source. No sample related ions were observed when the laser was off. The electrospray solvent spectra were subtracted from the LAESI spectra using the MassLynx 4.1 software (Waters Co., Milford, Mass.). EZinfo software (Version 2.0.0.0, Umetrics AB, Sweden) within the MarkerLynx application manager was used to perform multivariate statistical data analysis, such as orthogonal projections to latent structures discriminant analysis (OPLS-DA) to analyze the raw data. A two sample t-test, available in Origin software (OriginLab Co., Northampton, Mass.), was used to validate the differences in the normally distributed data sets, and the latter was verified with a normality test. Tentative peak assignments were made by comparing the accurate masses with those in the Plant Metabolic Network database (http://plantcyc.org/) and from previously published experimental results. In certain embodiments, the Extended Statistics module in the EZinfo software was used to perform OPLS-DA in order to identify and verify metabolites with strong variance between two subcellular components.

Figure 5:
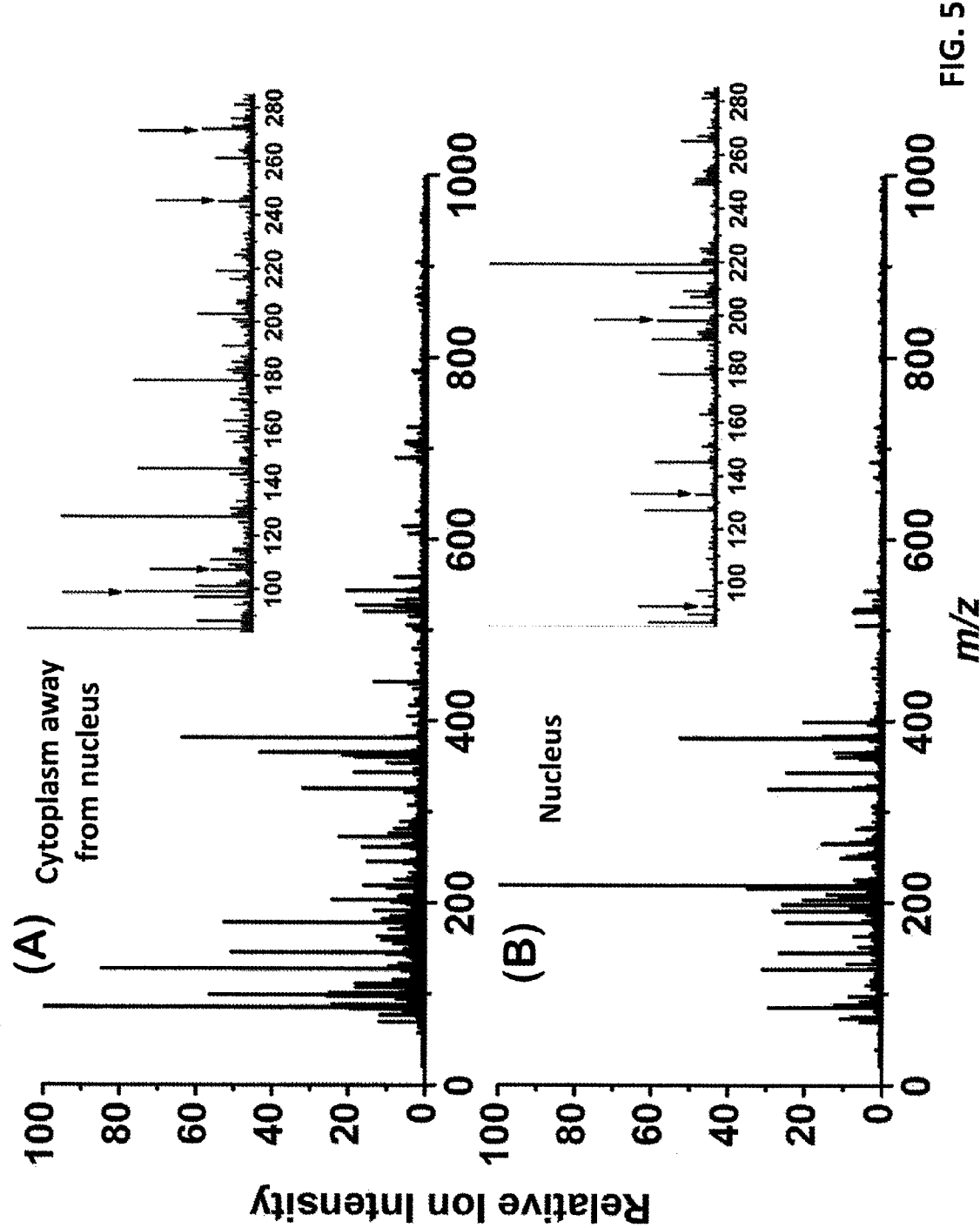
FIGS. 5A and B include representative mass spectra of a subcellular region lacking a nucleus (FIG. 5A) and a subcellular region including a nucleus (FIG. 5B) of an *A. cepa* epidermal cell after micro-dissection according to various embodiments described herein.

FIG. 5 includes LAESI spectra obtained by in vivo analysis of *A. cepa* cells according to certain embodiments described herein. An *A. cepa* cell was microdissected to expose the nucleus. The LAESI spectra of a subcellular region including the nucleus (bottom) and a subcellular region lacking the nucleus (top) show that each region comprises different metabolites and/or relative intensities. The LAESI spectra in the insets from the m/z 83-285 region show metabolites specific to either the nucleus, such as m/z 91.04, m/z 133.00, and m/z 198.08 (identified by arrows), or the subcellular region lacking the nucleus, such as m/z 98.97, m/z 245.02, and m/z 272.06 (identified by arrows).

Figure 6:
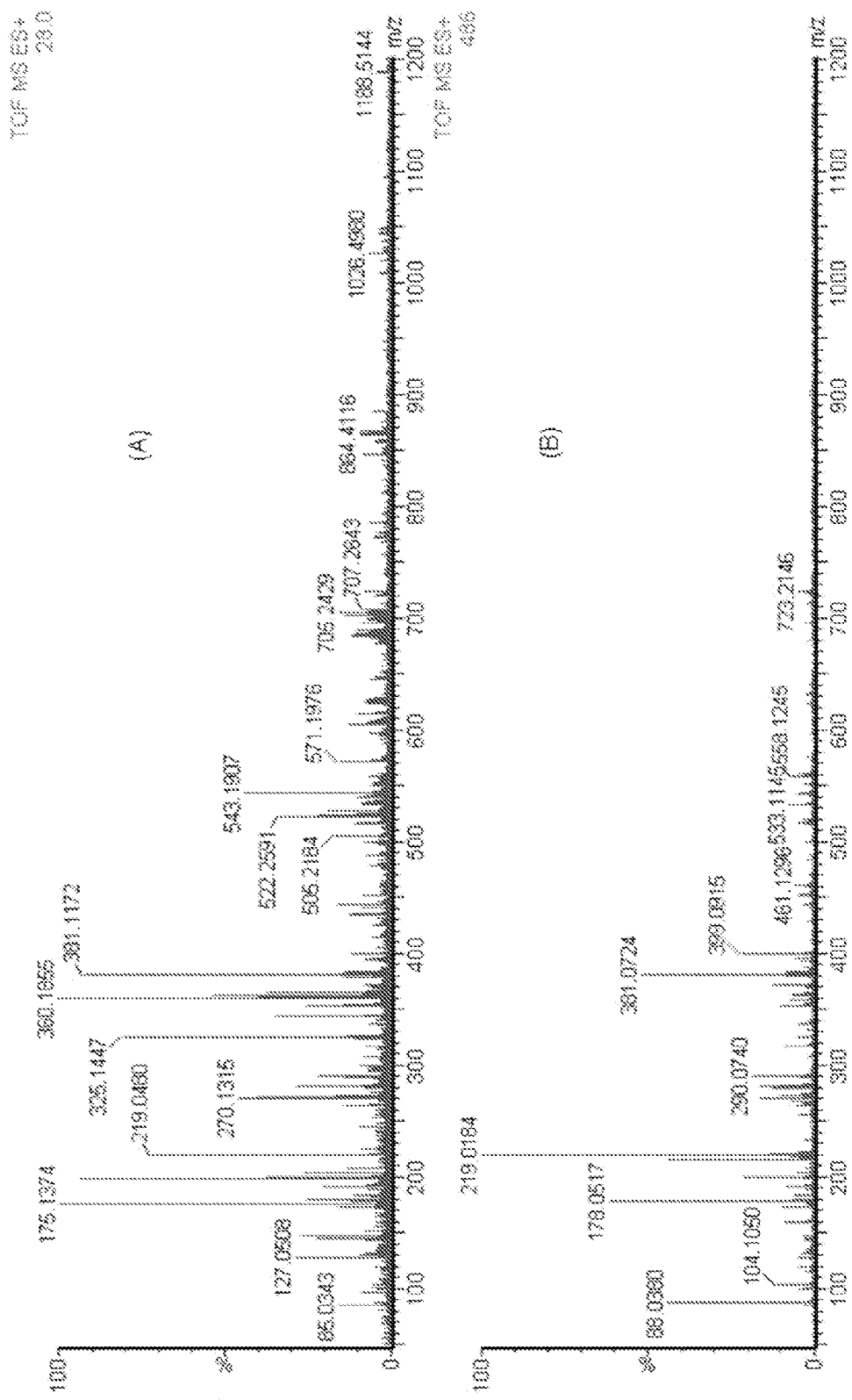
FIG. 6 includes representative mass spectra of a subcellular region including the nucleus (top) and a subcellular region lacking the nucleus (bottom) of an *A. cepa* epidermal cell after micro-dissection according to various embodiments described herein.
Figure 7:
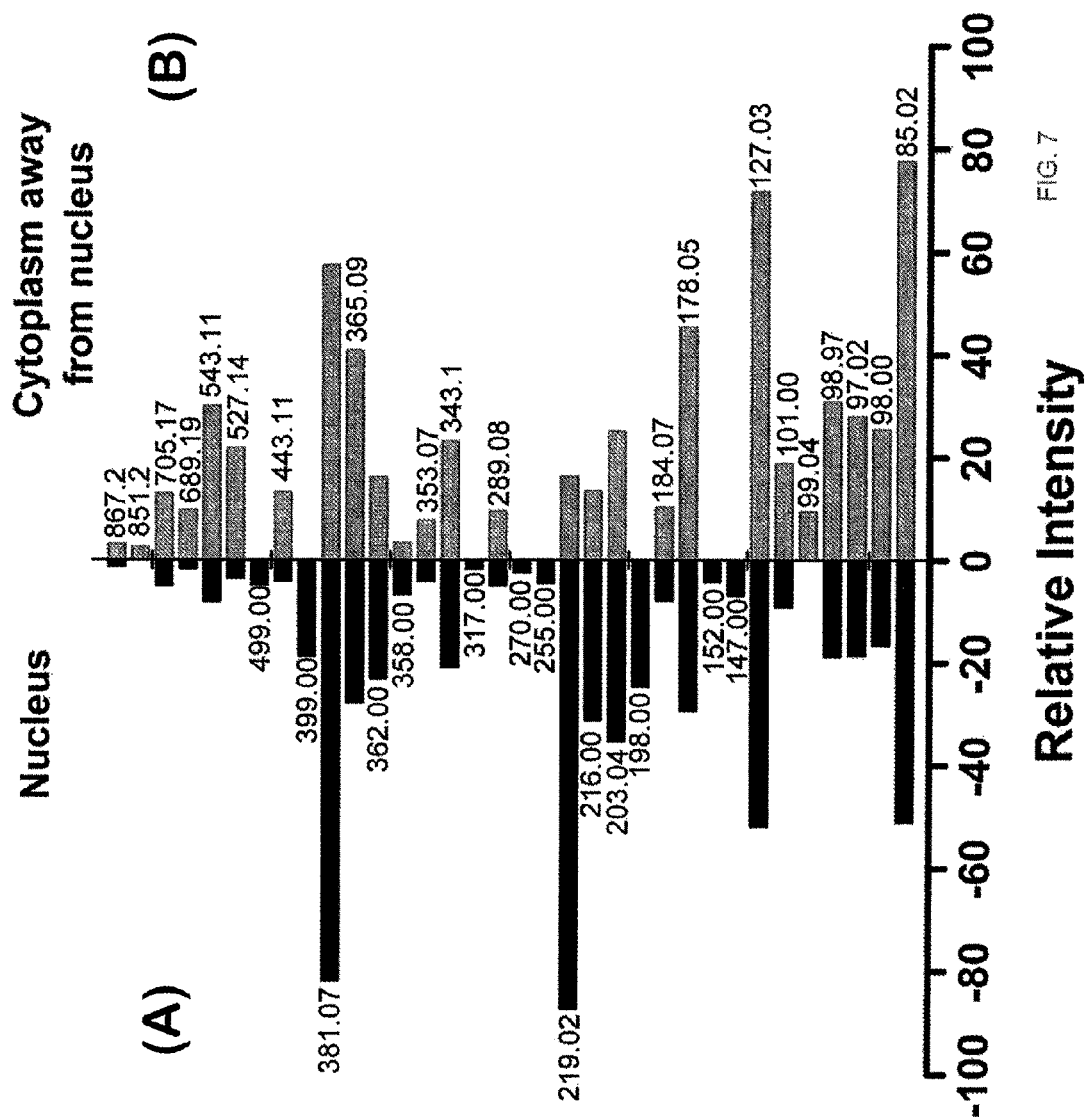
FIG. 7 includes a chart showing relative signal intensities for the nucleus (left) and the cytoplasm lacking the nucleus (right) from representative mass spectra of an *A. cepa* epidermal cell according to various embodiments described herein.

FIG. 6 includes LAESI spectra obtained after microdissection from a subcellular region including a nucleus (top) and a subcellular region lacking a nucleus (bottom) of an onion cell according to certain embodiments described herein. FIG. 7 includes a chart comparing the relative intensities of a subcellular region with a nucleus (left) and a subcellular region without a nucleus after microdissection (right).

Figure 8:
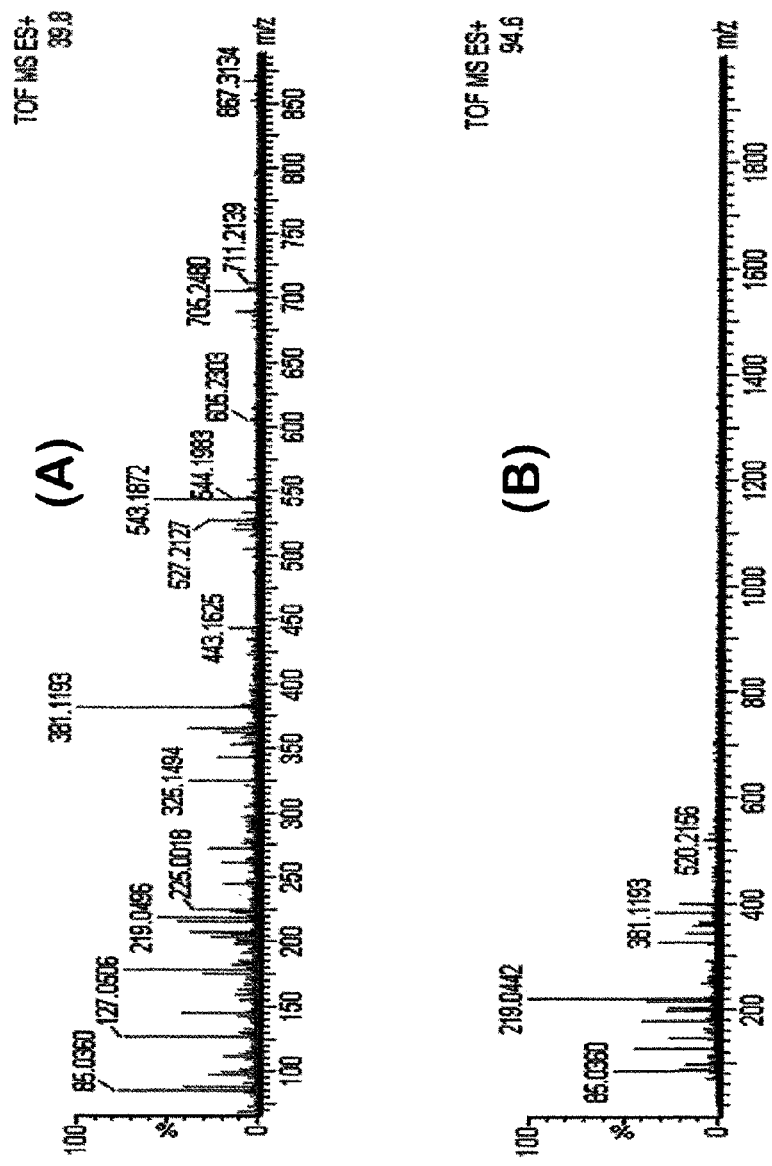
FIG. 8 includes representative mass spectra of the nucleus after micro-dissection (top) and the cytoplasm lacking the nucleus after micro-dissection (bottom) of an *A. cepa* epidermal cell according to various embodiments described herein.

FIG. 8 includes LAESI spectra obtained from a subcellular region including a nucleus (top) and a subcellular region lacking a nucleus (bottom) of an onion cell according to certain embodiments described herein.

Figure 9C:
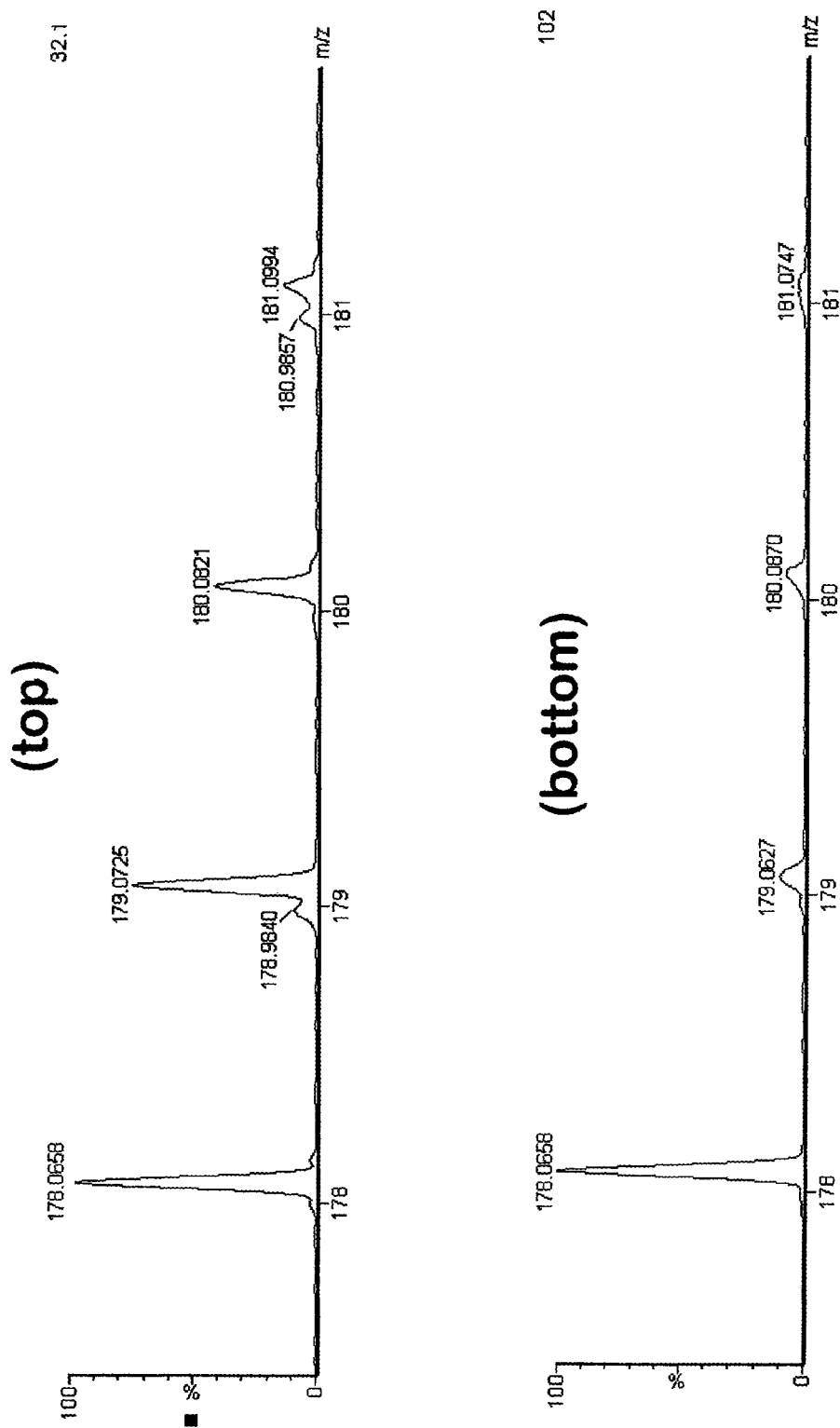

FIGS. 9A-C include LAESI spectra obtained from an onion cell exposed to deuterium oxide ($D_2O$) (top) and an onion cell not exposed to deuterium oxide ($D_2O$) (bottom). In this embodiment, epidermal cells were placed in deuterium oxide ($D_2O$) from 1 second to 60 seconds to allow the $D_2O$ to diffuse into the cell. Then the $D_2O$ was quickly rinsed off of the cell surface with water and LAESI-MS of the cell was recorded. The LAESI spectra indicate that the $D_2O$ transported into the cell through the cell wall and the cell membrane and hydrogen-deuterium exchange took place within the cell which is reflected in the isotope composition of the metabolites. FIG. 9B includes the isotope peak distribution for the m/z 365.1409 ion (sodiated sucrose) and the m/z 381.1121 ion (potassiated sucrose) of the $D_2O$ treated cell (top) exhibiting the increased isotope peaks due to the incorporation of up to eight deuterium atoms and untreated cell (bottom) exhibiting the natural isotope peak distribution. FIG. 9C includes the isotope peak distribution for the m/z 178.0658 ion (protonated alliin), a cysteine derivative present in onions, of the $D_2O$ treated cell (top) exhibiting the increased isotope peaks due to the incorporation of up to three deuterium atoms and the untreated cell (bottom) exhibiting the natural isotope peak distribution. These measurements enable investigation of proton and deuterium ion transport through the cell wall and cell membrane. They also provide information on the number of quickly exchangeable hydrogen atoms in the molecules inside the cell. Following the incorporation of various stable isotopes into the molecules inside a cell grown in isotope enriched medium by LAESI mass spectrometry also provides insight into cell metabolism on a single cell level.

Figure 10:
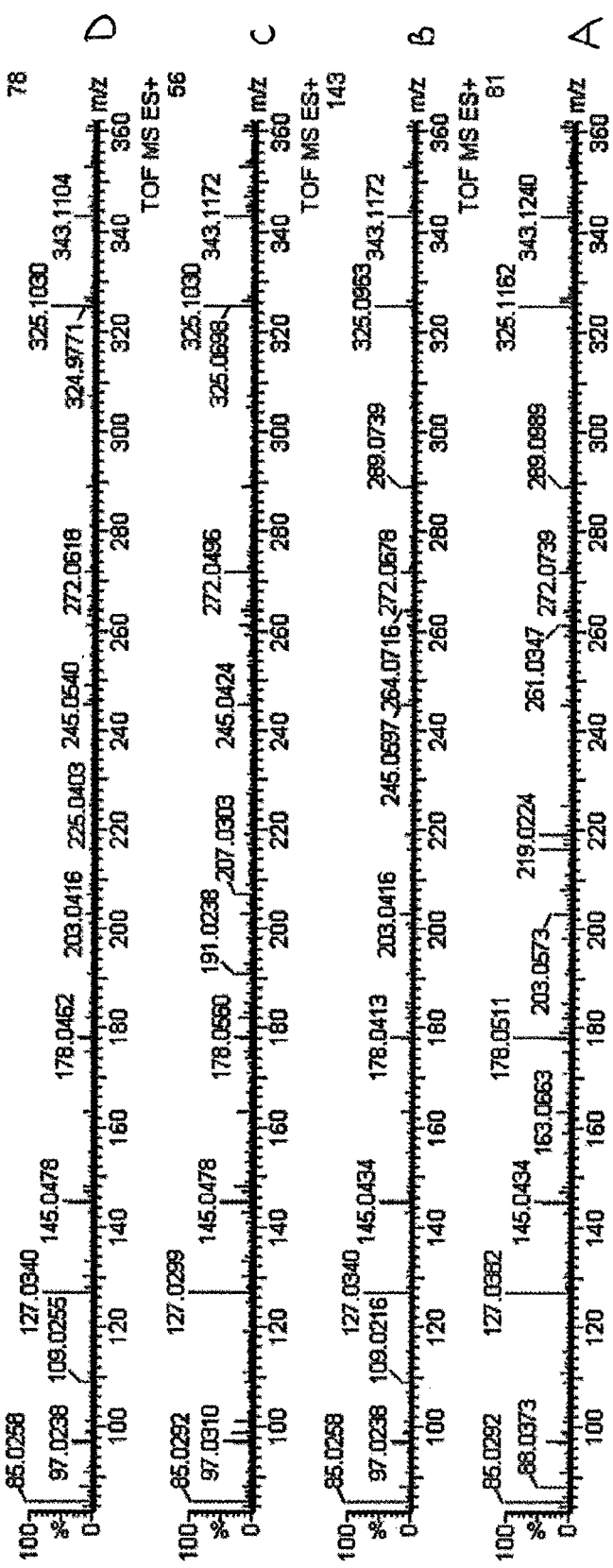
FIG. 10 includes representative mass spectra in the range of 80-360 m/z of various layers of an onion bulb (*A. cepa*) according to various embodiments described herein.
Figure 11:
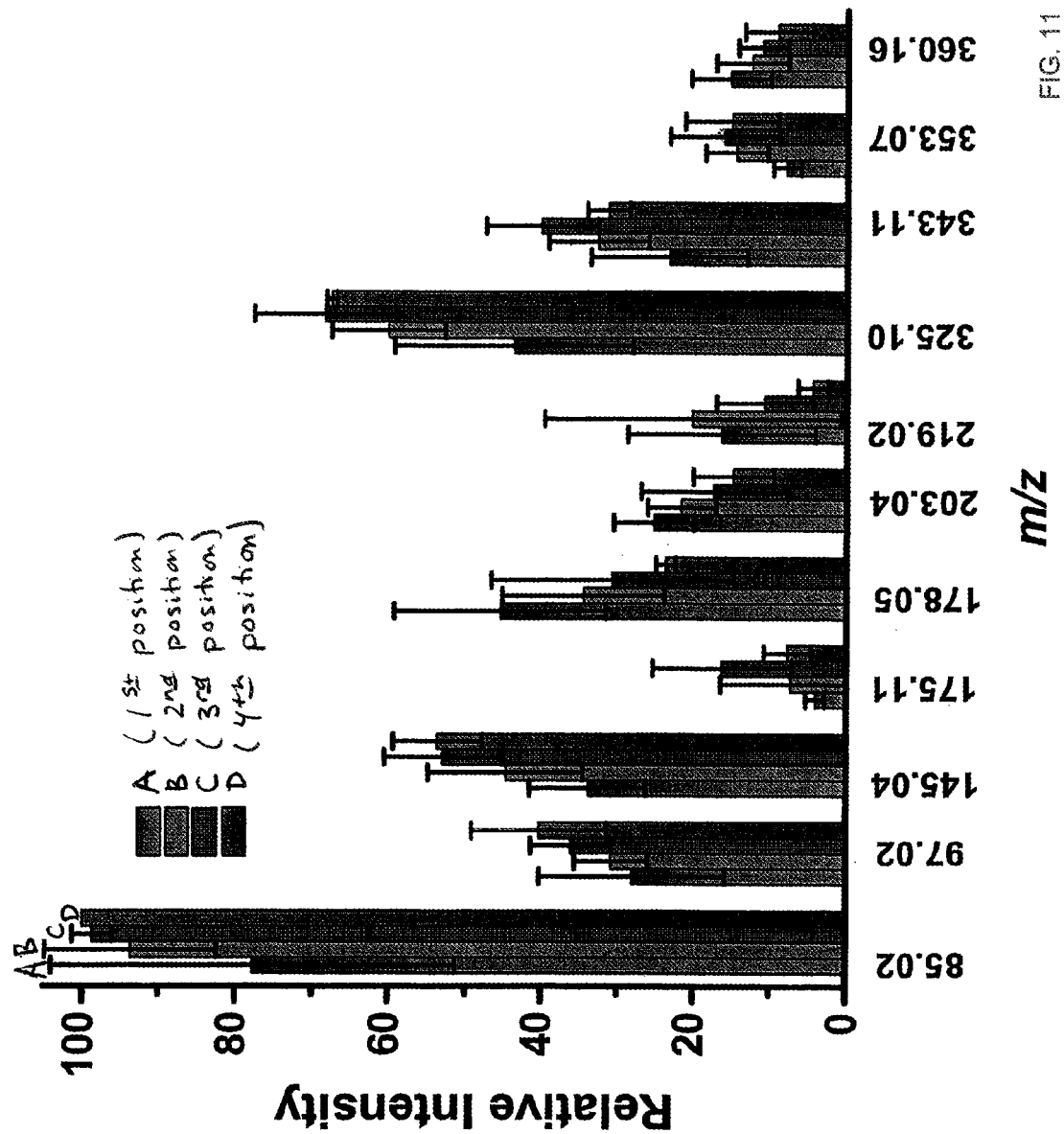
FIG. 11 includes a chart showing relative signal intensities of the representative mass spectra illustrated in FIG. 10.

FIG. 10 includes LAESI spectra in the range of 80-360 m/z obtained from subcellular regions lacking the nucleus of different leaf bases (layers) of the onion bulb according to certain embodiments described herein. The LAESI spectra include the second layer (A), third layer (B), fourth layer (C) and fifth layer (D). Each layer is associated with a different age. FIG. 11 includes a chart of representative metabolites of the second layer (A), third layer (B), fourth layer (C) and fifth layer (D). The m/z 85.02 ion is furanone, the m/z 145.04 ion is erythritol, the m/z 175.11 is arginine, the m/z 178.05 is alliin, the m/z 219.02 is a monosaccharide, and the m/z 325.10 is glucosan or dextrin unit. Each layer of the onion bulb may exhibit different relative signal intensities. FIG. 11 shows the changes in the relative signal intensities of selected ion of the mass spectra shown in FIG. 10.

Figure 12:
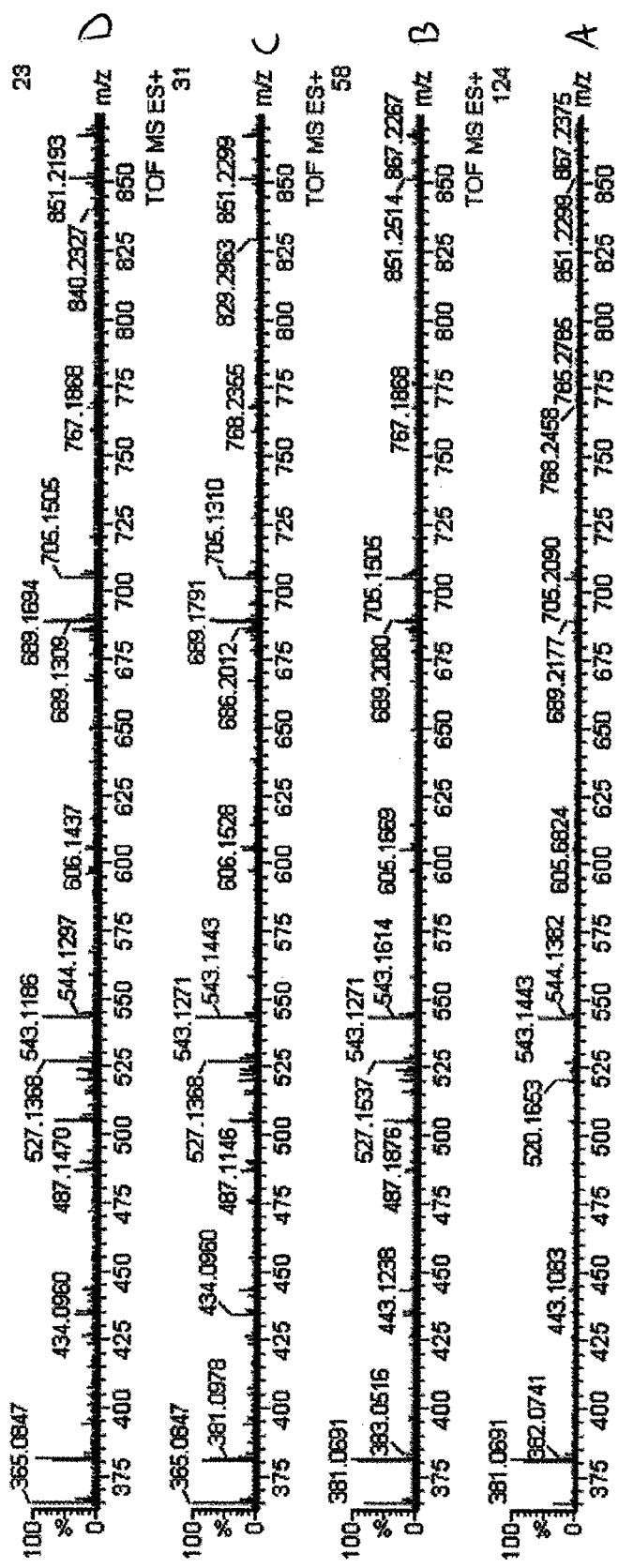
FIG. 12 includes representative mass spectra in the range of 360-875 m/z of various layers of an onion bulb (*A. cepa*) according to various embodiments described herein.
Figure 13:
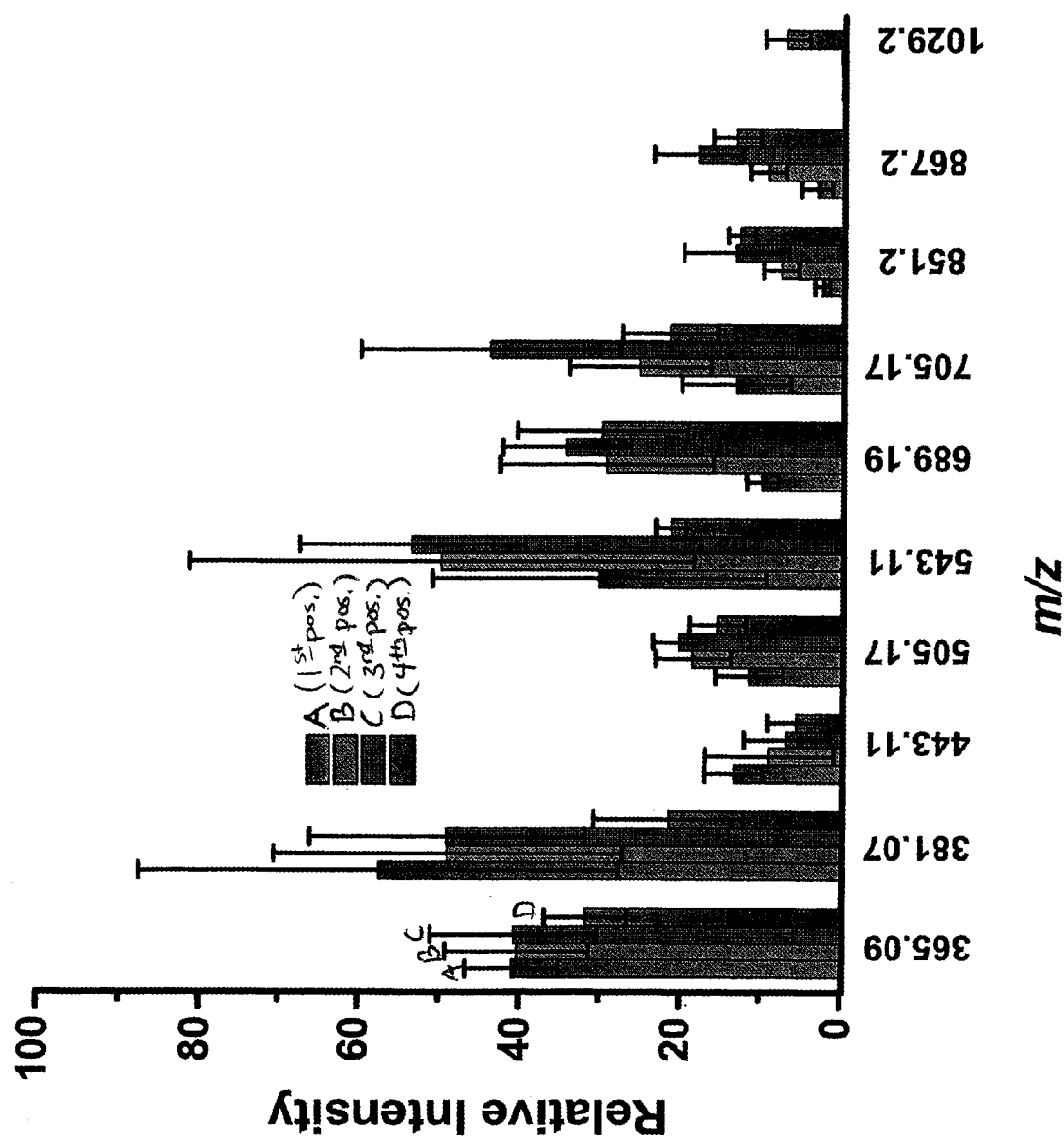
FIG. 13 includes a chart showing relative signal intensities of the representative mass spectra illustrated in FIG. 12.

FIG. 12 includes LAESI spectra in the range of 360-875 m/z obtained from subcellular regions lacking the nucleus of different leaf bases (layers) of the onion bulb according to certain embodiments described herein. The LAESI spectra include the second layer (A), third layer (B), fourth layer (C) and fifth layer (D). FIG. 13 includes a chart of ion abundances for representative metabolites of the second layer (A), the third layer (B), the fourth layer (C) and fifth layer (D). The m/z 381.07 ion is disaccharide, the m/z 543.11 ion is trisaccharide, the m/z 705.17 is tetrasaccharide, the m/z 867.2 is pentasaccharide, and the m/z 1029.2 is a hexasaccharide.

Figure 14:
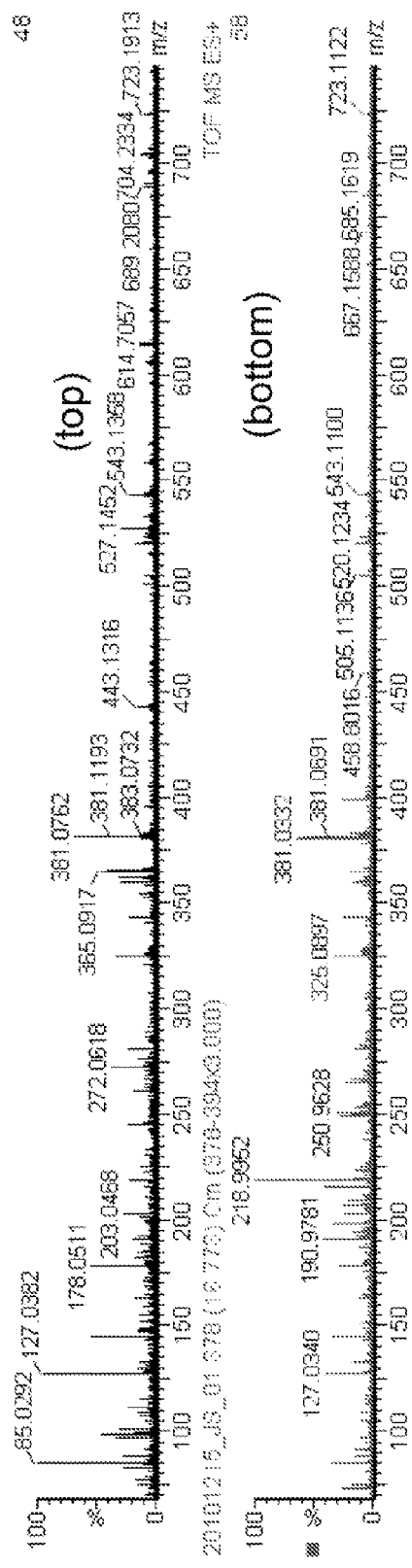
FIG. 14 includes representative mass spectra of the cytoplasm lacking the nucleus (top) and the nucleus (bottom) of an *A. cepa* epidermal cell according to various embodiments described herein.

FIG. 14 includes LAESI spectra obtained from a subcellular region lacking a nucleus (top) and a subcellular region including a nucleus (bottom) from an onion cell according to certain embodiments described herein.

Figure 15:
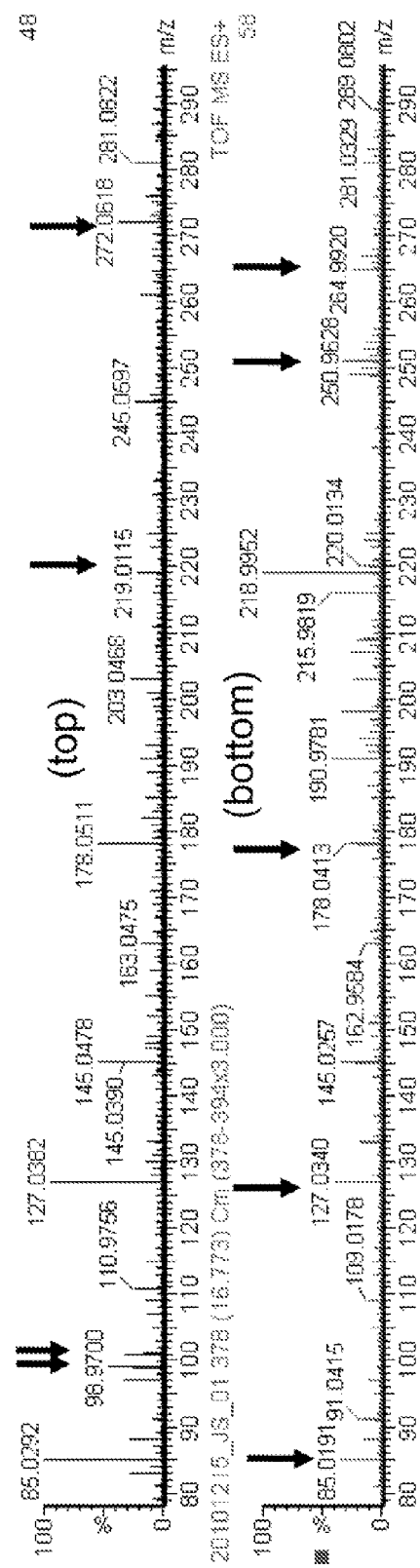
FIG. 15 includes representative mass spectra in the range of 80-300 m/z of the cytoplasm lacking the nucleus (top) and the nucleus (bottom) of an *A. cepa* epidermal cell according to various embodiments described herein.

FIG. 15 includes LAESI spectra in the range of 80-300 m/z obtained from a subcellular region lacking a nucleus (top) and a subcellular region including a nucleus (bottom) from an onion cell according to certain embodiments described herein. Arrows in the spectra point to ions with different intensities in the two subcellular regions and include ions at m/z 85.02, m/z 98.97, m/z 127.03, m/z 178.04, m/z 219.01, m/z 250.96, m/z 264.99, and m/z 272.06.

Figure 16:
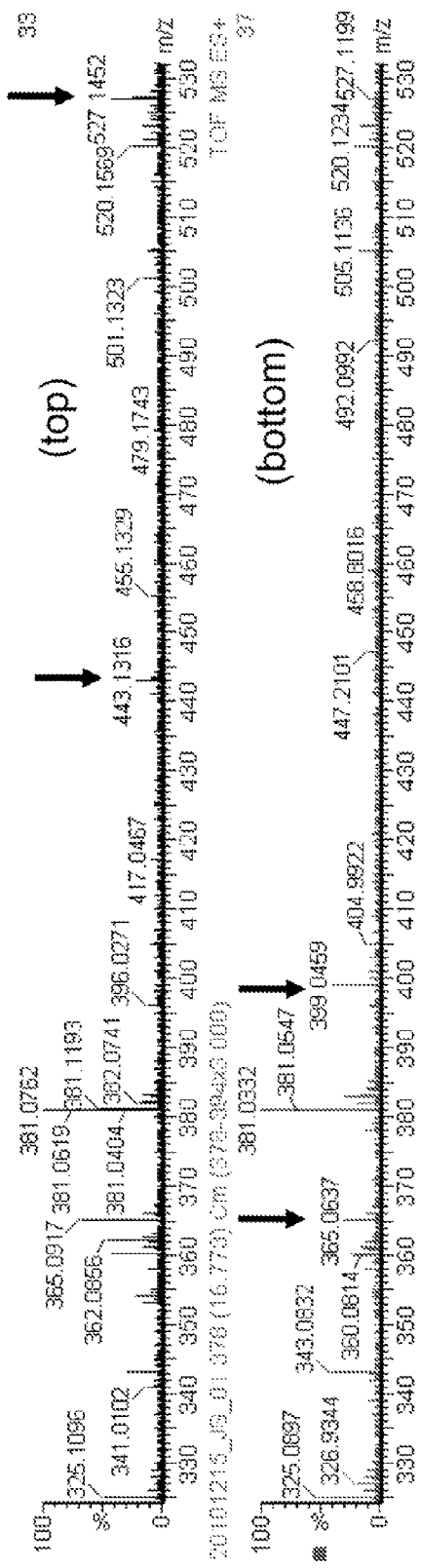
FIG. 16 includes representative mass spectra in the range of 324-532 m/z of the cytoplasm lacking the nucleus (top) and the nucleus (bottom) of an *A. cepa* epidermal cell according to various embodiments described herein.

FIG. 16 includes LAESI spectra in the range of 320-530 m/z obtained from a subcellular region lacking a nucleus (top) and a subcellular region including a nucleus (bottom) from an onion cell according to certain embodiments described herein. Arrows in the spectra point to ions with different intensities in the two subcellular regions and include ions at m/z 365.06, m/z 399.04, m/z 443.13, and m/z 527.14.

Figure 17:
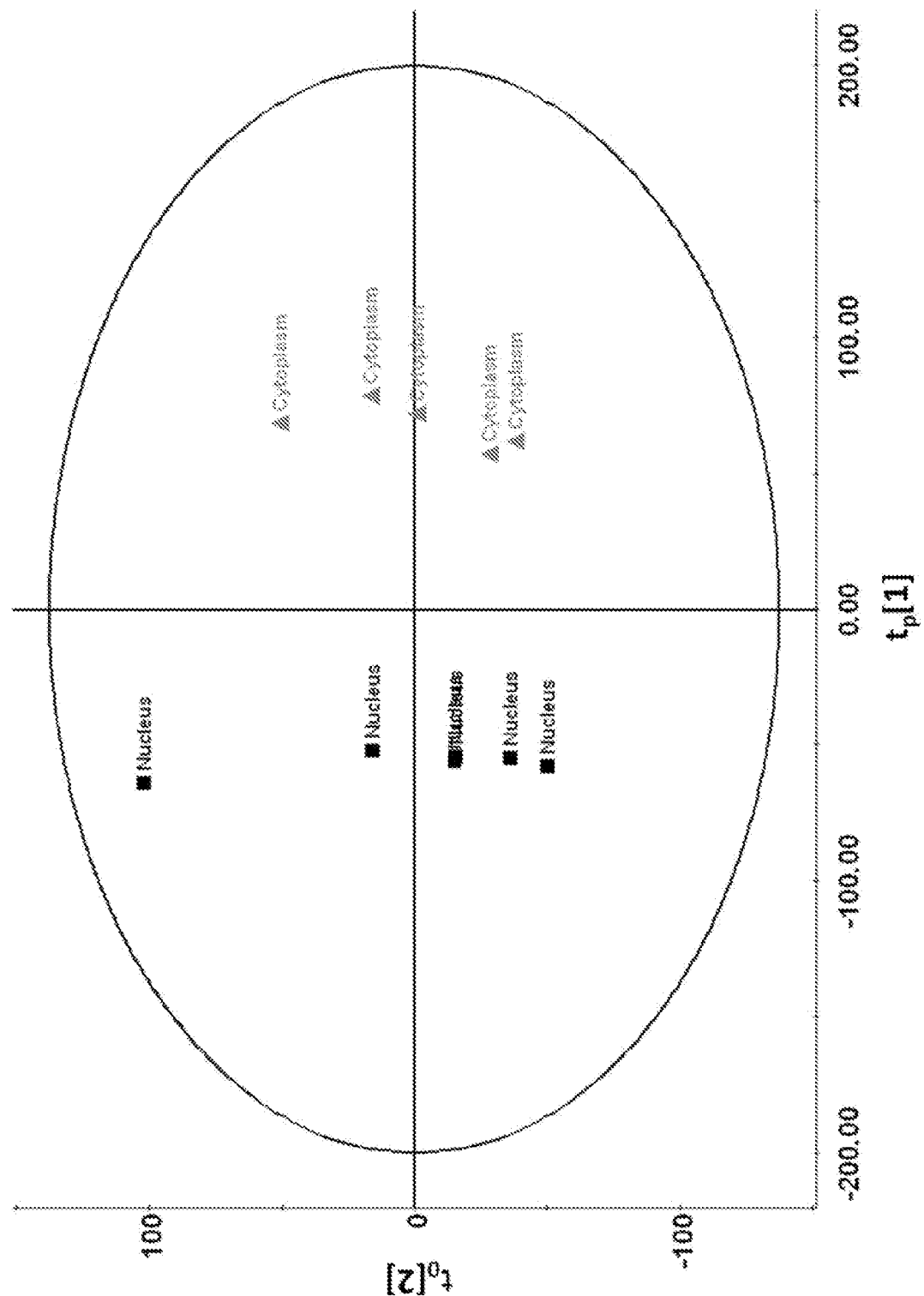
FIG. 17 includes a score plot of representative mass spectra of the cytoplasm lacking the nucleus (▲) and the nucleus (■) of an *A. cepa* epidermal cell according to various embodiments described herein.
Figure 18:
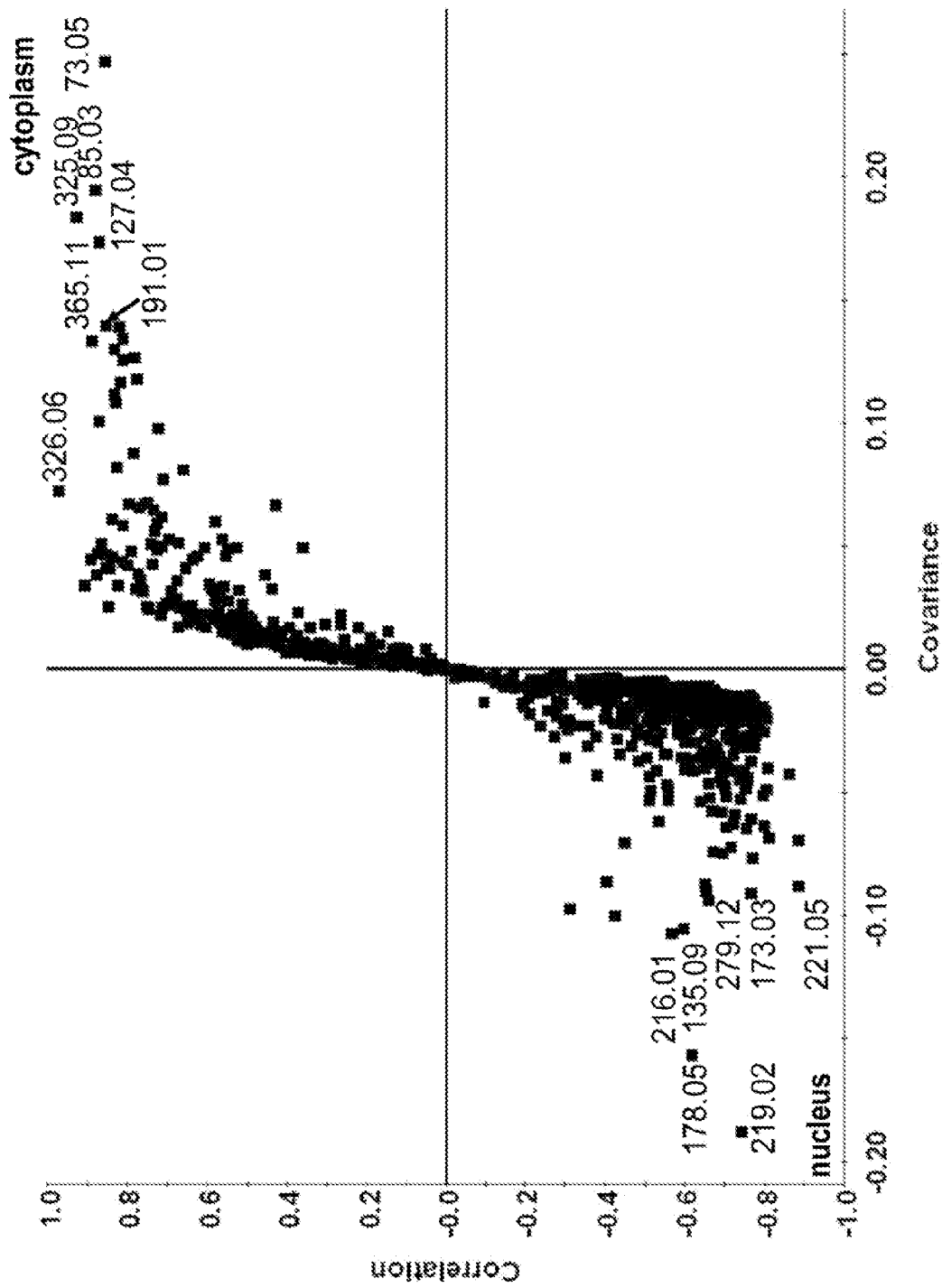
FIG. 18 includes an S-plot plotting the correlation vs. covariance of representative mass spectra of the cytoplasm lacking the nucleus and the nucleus of an *A. cepa* epidermal cell according to various embodiments described herein.

FIGS. 17-18 include charts of multivariate statistical analyses of a subcellular region including a nucleus and a subcellular region lacking a nucleus (cytoplasm). FIG. 17 is a score plot obtained by orthogonal projections to latent structures discriminant analysis (OPLS-DA) and shows that the two subcellular regions are completely separated in the first predictive component, $t_p[1]$, and variations within the subcellular regions are observed in the orthogonal component, $t_p[2]$. All the points fell well within the Hotelling $T^2$ range with a significance level of $p=0.05$ represented by the ellipse in FIG. 17, thus no subcellular regions were misclassified. An S-plot, based on the relationship between correlation and covariance produced by OPLS-DA, was used to provide the identification of metabolites responsible for most of the variance between the spectra of the cell nucleus and cytoplasm away from the nucleus, as shown by the m/z values marked in the S-plot presented in FIG. 18.

Figure 19:
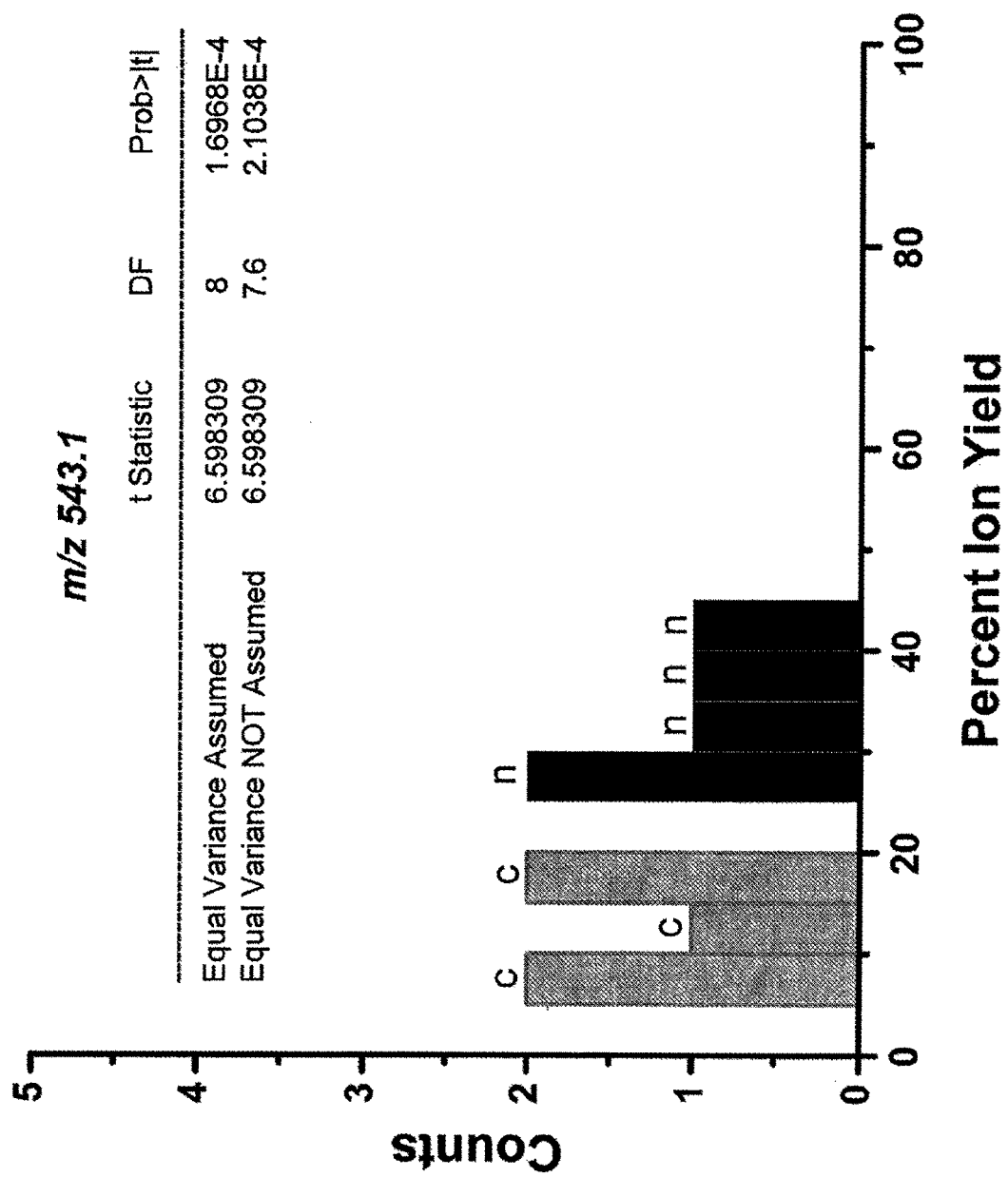
FIGS. 19-21 include histograms plotting the counts vs. percent ion yield of various ions from the cytoplasm lacking the nucleus (c) and the nucleus (n) of an *A. cepa* epidermal cell according to various embodiments described herein.

FIG. 19 includes a chart of counts v. percent ion yield for the m/z 543.1 ion for a subcellular region including a nucleus (n) and subcellular region lacking a nucleus (c). Table 3 shows the t-test statistics for the m/z 543.1 ion. The null hypothesis is that the difference between the population means in the two regions is zero. At the 0.05 level, the difference between the population means is statistically significant and, thus the null hypothesis is rejected, i.e., the m/z 543.1 ion yields in the two regions are different.

TABLE 3

|  | t statistic | Degree of freedom | Probability > \|t\| |
| --- | --- | --- | --- |
| Equal variance assumed | 6.60 | 8 | $1.70 \times 10^{-4}$ |
| No equal variance assumed | 6.60 | 7.62 | $2.10 \times 10^{-4}$ |

Figure 20:
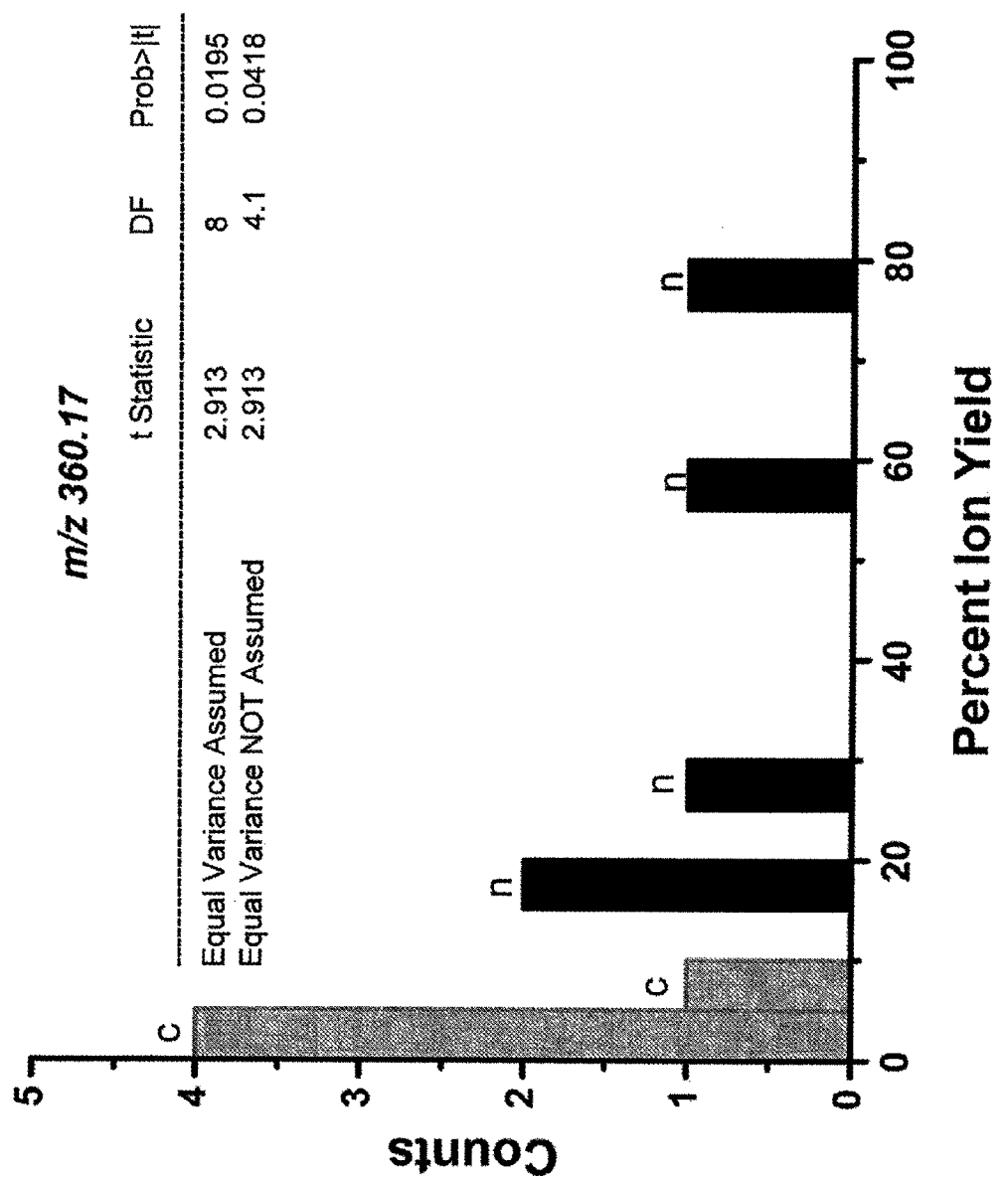

FIG. 20 includes a chart of counts v. percent ion yield for the m/z 360.17 ion for a subcellular region including a nucleus (n) and subcellular region lacking a nucleus (c).

Figure 21:
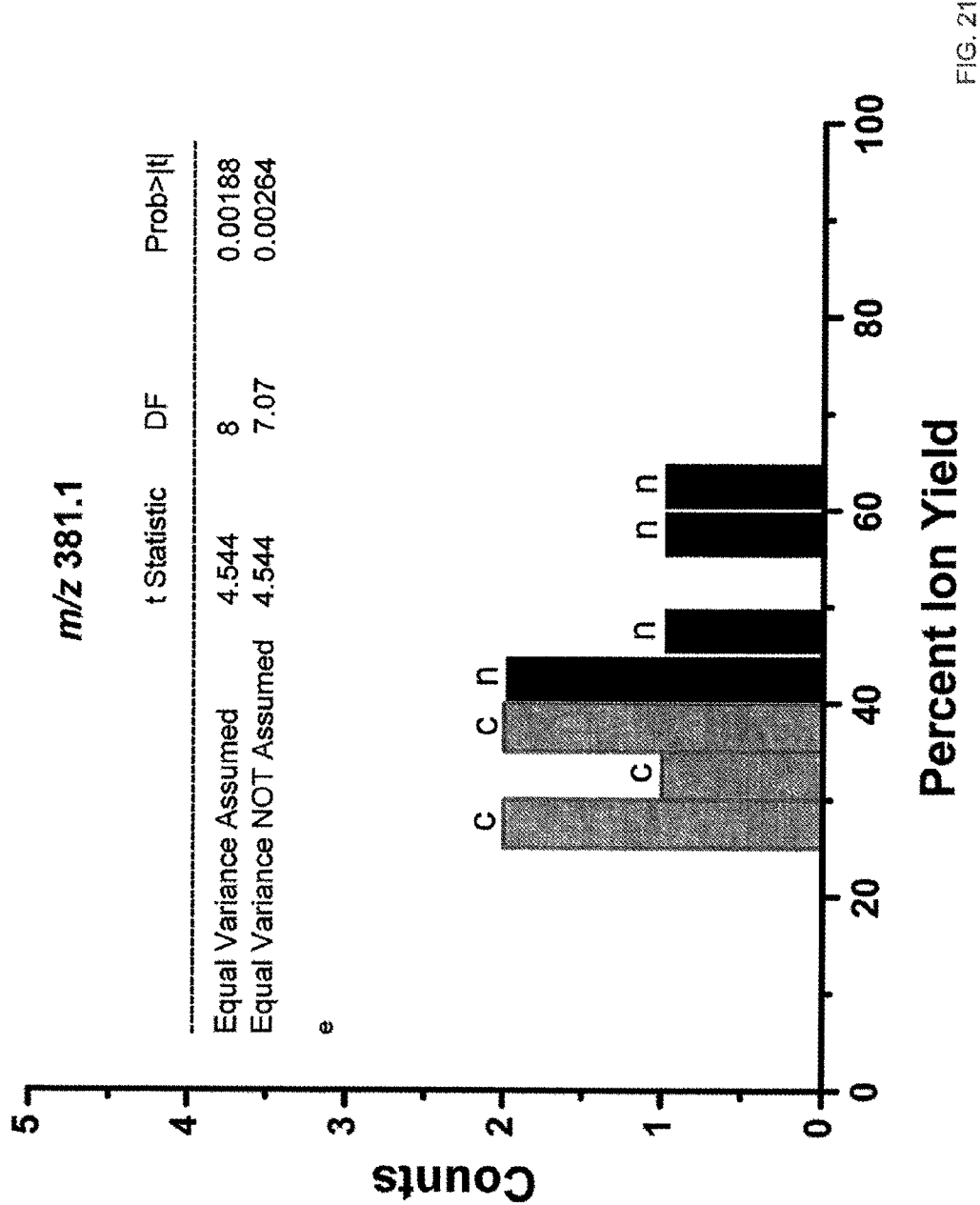

FIG. 21 includes a chart of counts v. percent ion yield for the m/z 381.1 ion for a subcellular region including a nucleus (n) and subcellular region lacking a nucleus (c). Table 4 shows the t-test statistics for the m/z 381.1 ion. The null hypothesis is that the difference between the population means in the two regions is zero. At the 0.05 level, the difference between the population means is statistically significant and, thus the null hypothesis is rejected, i.e., the m/z 381.1 ion yields in the two regions are different.

TABLE 4

|  | t statistic | Degree of freedom | Probability > \|t\| |
| --- | --- | --- | --- |
| Equal variance assumed | 4.54 | 8 | $1.88 \times 10^{-3}$ |
| No equal variance assumed | 4.54 | 7.07 | $2.64 \times 10^{-3}$ |

FIG. 22 includes mass spectra obtained from an *A. cepa* cell lacking microdissection. The first laser pulse (1$^{st}$ Shot) did not generate a detectable mass spectrometric signal. Without wishing to be bound to any particular theory, it is believed that no mass spectrometric signal was detectable because the first laser pulse did not rupture the cell wall. The second laser pulse (2$^{nd}$ Shot), third laser pulse (3$^{rd}$ Shot) and fourth laser pulse (4$^{th}$ Shot) generated detectable mass spectrometric signals. Without wishing to be bound to any particular theory, it is believed that the cell wall broke during the second laser pulse resulting in a detectable mass spectrometric signal. The mass spectra for the second and fourth laser pulses included similar ions and relative abundances. As shown in FIG. 22, the mass spectra for the third laser pulse included higher relative abundances for certain ions, such as, for example, the m/z 381 ion. The m/z 203 and 381 ions are believed to be sodiated glucose and potassiated sucrose, respectively. Without wishing to be bound to any particular theory, it is believed that the increase in the m/z 381 ion is related to the internal inhomogeneity of the cell. For example, it is known that vacuoles, which are organelles that may occupy from 30% to 80% of the cell volume in plants, may store significant amounts of sucrose. It is believed that the third laser pulse induced the rupture of the vacuolar membrane and released/ablated the content of the vacuole.

No detectable mass spectrometric signal was generated after the fourth laser pulse. Without wishing to be bound to any particular theory, it is believed that the lack of detectable mass spectrometric signal after the fourth laser pulse may be related to the removal of the cytoplasm by the previous laser pulses and/or drying of the cell due to evaporation of its water content during the 40-50 s course of the experiment. To assess the effect of depleting the cytoplasm and evaporating the water content of the cell, bursts of 10 to 100 laser pulses separated by 10 s intermissions were delivered to an *A. cepa* cell. No detectable mass spectrometric signal was generated after 40-50 laser pulses. No detectable mass spectrometric signal was generated after 40-50 s.

All documents cited herein are incorporated herein by reference, but only to the extent that the incorporated material does not conflict with existing definitions, statements, or other documents set forth herein. To the extent that any meaning or definition of a term in this document conflicts with any meaning or definition of the same term in a document incorporated by reference, the meaning or definition assigned to that term in this document shall govern. The citation of any document is not to be construed as an admission that it is prior art with respect to this application.

While particular embodiments of LAESI and LAESI-MS have been illustrated and described, it would be obvious to those skilled in the art that various other changes and modifications can be made without departing from the spirit and scope of the invention. Those skilled in the art will recognize, or be able to ascertain using no more than routine experimentation, numerous equivalents to the specific apparatuses and methods described herein, including alternatives, variants, additions, deletions, modifications and substitutions. This application including the appended claims is therefore intended to cover all such changes and modifications that are within the scope of this application.

What is claimed is:

1. A method of laser ablation electrospray ionization mass spectrometry, the method comprising:
   micro-dissecting a cell comprising at least one of a cell wall and a cell membrane to expose in the cell at least one subcellular component having a water content;
   ablating in the cell the at least one subcellular component by a mid-infrared laser pulse to form an ablation plume;
   intercepting the ablation plume by an electrospray plume to form ions; and
   detecting the ions by mass spectrometry;
   wherein the laser pulse has a laser energy that is absorbed by the water.

2. The method of claim 1, wherein micro-dissecting the cell comprises cutting at least a portion of the at least one of a cell wall and a cell membrane by at least one of a microdissection tool, an optical tweezer, and at least one laser pulse.

3. The method of claim 1, wherein micro-dissecting the cell comprises cutting at least a portion of the at least one of a cell wall and a cell membrane by a microdissection tool comprising a tungsten needle having a tip diameter of less than 1 µm to 5 µm.

4. The method of claim 1, wherein micro-dissecting the cell comprises cutting at least a portion of the at least one of a cell wall and a cell membrane by an optical tweezer comprising a laser, a beam expander, beam steering optics comprising at least one of a mirror, a lens, and a condenser.

5. The method of claim 1, wherein micro-dissecting the cell comprises irradiating the at least one of a cell wall and a cell membrane with at least one laser pulse having a wavelength of 100 nm to 8 µm, a diameter of 0.5-20 µm, and a pulse length of less than one picosecond to 100 ns under ambient conditions.

6. The method of claim 5, wherein the laser pulse has a wavelength of 800 nm, a diameter of 1 µm, and a pulse length of 200 fs.

7. The method of claim 5, wherein the laser pulse has a wavelength of 100 nm to 400 nm, a diameter of 1 µm to 5 µm, and a pulse length of 1 ns to 100 ns.

8. The method of claim 1, wherein micro-dissecting the cell comprises irradiating the cell with a laser pulse by a microdissection optical fiber comprising a core diameter, a tip radius of curvature, a tip angle of inclination, and a tip distance from the cell.

9. The method of claim 8, wherein the microdissection optical fiber core diameter is 15-450 µm, the microdissection optical fiber tip radius of curvature is 0.1-10 lam, the microdissection optical fiber tip angle of inclination is 15-90°, and the microdissection optical fiber tip distance is 0-30 µm.

10. The method of claim 8, wherein ablating the at least one subcellular component comprises irradiating the cell with the laser pulse by an ablation optical fiber comprising a core diameter, a tip radius of curvature, a tip angle of inclination, and a tip distance from the cell.

11. The method of claim 10, wherein the ablation optical fiber core diameter is 15-450 µm, the ablation optical fiber tip radius of curvature is 0.1-25 µm, the ablation optical fiber tip angle of inclination is 15-90°, and the ablation optical fiber tip distance is 0-30 µm.

12. The method of claim 1, wherein micro-dissecting the cell comprises generating an opening in the at least one of a cell wall and a cell membrane having a diameter of 1-50 µm.

13. The method of claim 1, wherein the at least one subcellular component comprises at least one exchangeable hydrogen, and exchanging the at least one exchangeable hydrogen with at least one isotope.

14. The method of claim 1 comprising staining the at least one subcellular component.

15. The method of claim 1 comprising positioning the cell on a temperature controlled sample stage in an environmental chamber having a temperature between and 40° C. and a relative humidity of 10-90%.

16. The method of claim 1, wherein the cell is an eukaryotic cell having a smallest dimension of 1 μm to 100 μm, 25 μm to 100 μm, 10 μm to 25 μm, and 1 μm to 10 μm.

17. The method of claim 1, wherein the at least one subcellular component comprises one or more of cytoplasm, a nucleus, a mitochondrion, a chloroplast, a ribosome, an endoplasmic reticulum, a Golgi apparatus, a lysosome, a proteasome, a secretory vesicle, a vacuole, and a microsome.

18. An in situ method of laser ablation electrospray ionization mass spectrometry of a sample comprising at least one subcellular component having a water content, the method comprising:
   micro-dissecting the sample to expose in the cell the at least one subcellular component;
   ablating in the cell the exposed at least one subcellular component by a mid-infrared laser pulse to form an ablation plume;
   intercepting the ablation plume by an electrospray plume to form ions; and
   detecting the ions by mass spectrometry;
   wherein the laser pulse has a laser energy that is absorbed by the water.

19. The method of claim 18, wherein the sample comprises at least one of a cell wall and a cell membrane, and micro-dissecting the sample comprises at least one of piercing, cutting, rupturing, separating and removing at least a portion of the at least one of a cell wall and a cell membrane.

20. The method of claim 19 comprising at least one of piercing, cutting, rupturing, separating and removing at least a portion of a membrane enclosing the at least one subcellular component.

* * * * *